United States Patent [19]

Bramm et al.

[11] Patent Number: 4,944,748

[45] Date of Patent: * Jul. 31, 1990

[54] MAGNETICALLY SUSPENDED AND ROTATED ROTOR

[76] Inventors: Gunter W. Bramm, Luisen Strasse 49, 8000 Munchen 2, Fed. Rep. of Germany; Don B. Olsen, 8832 Blue Jay La., Salt Lake City, Utah 84121

[*] Notice: The portion of the term of this patent subsequent to May 26, 2004 has been disclaimed.

[21] Appl. No.: 193,180

[22] Filed: May 9, 1988

Related U.S. Application Data

[63] Continuation of Ser. No. 914,486, Oct. 12, 1986, which is a continuation of Ser. No. 720,081, Apr. 4, 1985.

[51] Int. Cl.⁵ .................................................. A61M 1/10
[52] U.S. Cl. ........................................ 623/3; 417/356; 416/111
[58] Field of Search ............................ 623/3; 416/111; 417/356

[56] References Cited

U.S. PATENT DOCUMENTS

| | | |
|---|---|---|
| Re. 27,849 | 12/1973 | Wortman . |
| 1,105,967 | 8/1914 | Davidson . |
| 1,711,045 | 4/1929 | Davis . |
| 2,263,515 | 11/1941 | Pezzillo . |
| 2,319,730 | 5/1943 | Garraway . |
| 2,500,400 | 3/1950 | Cogswell . |
| 2,535,695 | 12/1950 | Pezzillo, Jr. . |
| 2,827,856 | 3/1958 | Zozulin . |
| 3,194,165 | 7/1965 | Sorlin . |
| 3,433,163 | 3/1969 | Sheets . |
| 3,647,324 | 3/1972 | Rafferty et al. . |
| 3,846,050 | 11/1974 | Laing . |
| 3,938,913 | 2/1976 | Isenberg et al. . |
| 3,957,389 | 5/1976 | Rafferty et al. . |
| 3,970,408 | 7/1976 | Rafferty et al. . |
| 4,173,796 | 11/1979 | Jarvik . |
| 4,213,207 | 7/1980 | Wilson . |
| 4,382,199 | 5/1983 | Isaacson .............................. 416/111 |
| 4,518,317 | 5/1985 | Inoue . |
| 4,523,896 | 6/1985 | Lhenry et al. . |
| 4,688,998 | 8/1987 | Olsen et al. .......................... 417/356 |

FOREIGN PATENT DOCUMENTS

| | | |
|---|---|---|
| 1202392 | 10/1965 | Fed. Rep. of Germany . |
| 2341766 | 2/1975 | Fed. Rep. of Germany . |
| 2420825 | 11/1975 | Fed. Rep. of Germany . |
| 2457783 | 6/1976 | Fed. Rep. of Germany . |
| 2515608 | 9/1976 | Fed. Rep. of Germany . |
| 2177339 | 11/1973 | France . |
| 361209 | 7/1938 | Italy . |

OTHER PUBLICATIONS

"An Instrumental Approach to In Vivo Hemocompatibility Assessment: Development of the Intravascular Magnetic Suspension of A Test Device", by D. M. Lederman, R. D. Cumming, H. E. Petschek, T. H. Chiu, E. Nyilas, and E. W. Salzman, vol. 283, pp. 524–535, Feb. 10, 1977, 24894.

Primary Examiner—Randall L. Green
Assistant Examiner—Stephanie L. Iantorno
Attorney, Agent, or Firm—Dunlap, Codding, Peterson & Lee

[57] ABSTRACT

The impellor of a blood pump is supported by permanent magnets on the impellor and pump housing and stabilized by an electromagnet on the housing. A control circuit supplies current to the electromagnet to maintain the axial position of the impellor at a control position in which the impellor is in mechanical equilibrium under permanent magnet forces and static axial forces on the impellor to minimize energy consumption in the support of the impellor. The impellor is rotated magnetically and stator coils in the housing are supplied with electric currents having a frequency and amplitude adjusted in relation to blood pressure at the pump inlet to match the flow characteristics of the pump to physiological characteristics of the natural heart. A cavity is formed in the impellor to match the average specific gravity of the impellor and portions of the suspension and drive systems thereon to the specific gravity of blood to further minimize power consumption by the pump. A valve member can be formed on the impellor to mate with a restriction in the pump inlet for pumps used to assist the pumping action of the natural heart.

10 Claims, 14 Drawing Sheets

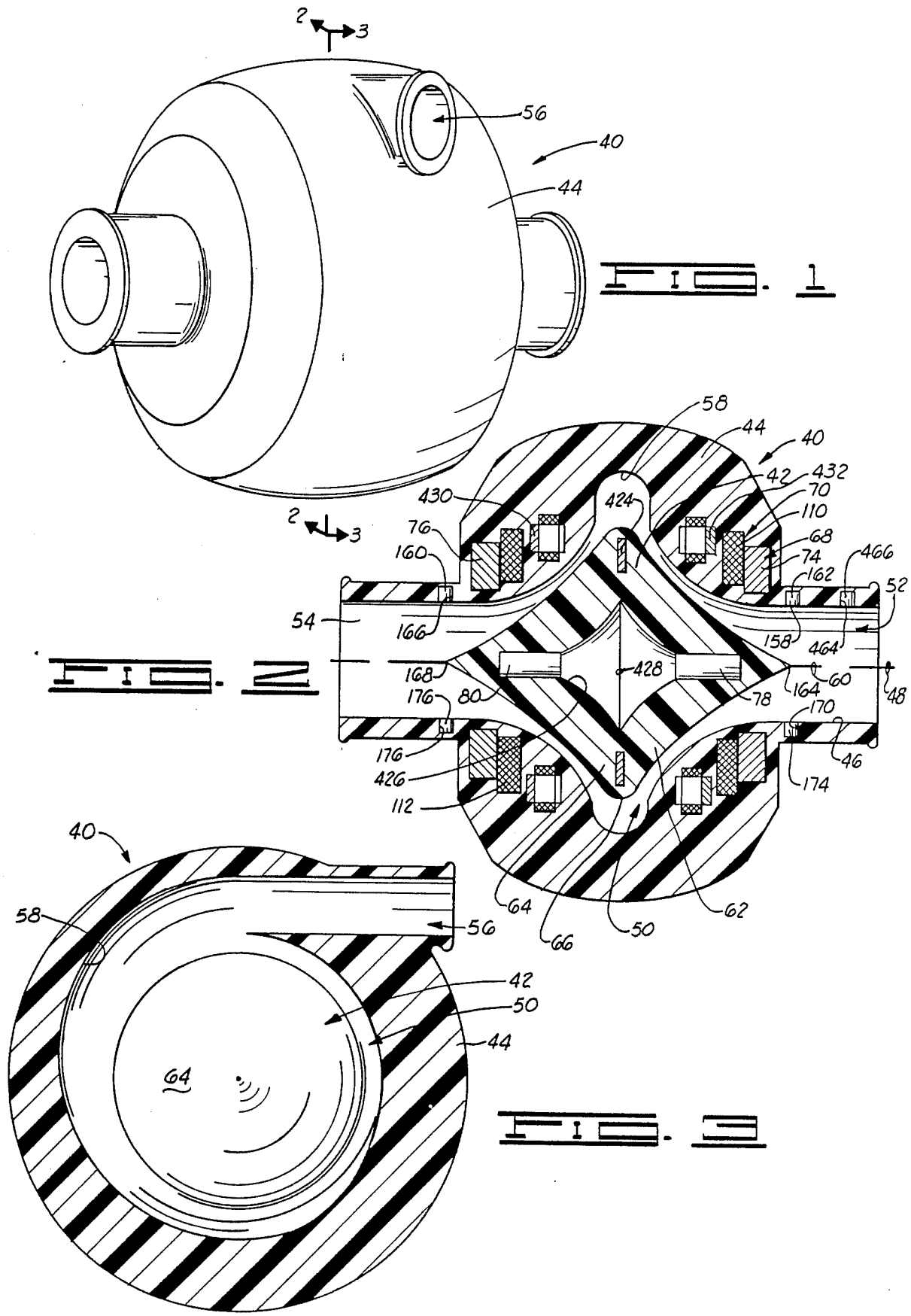

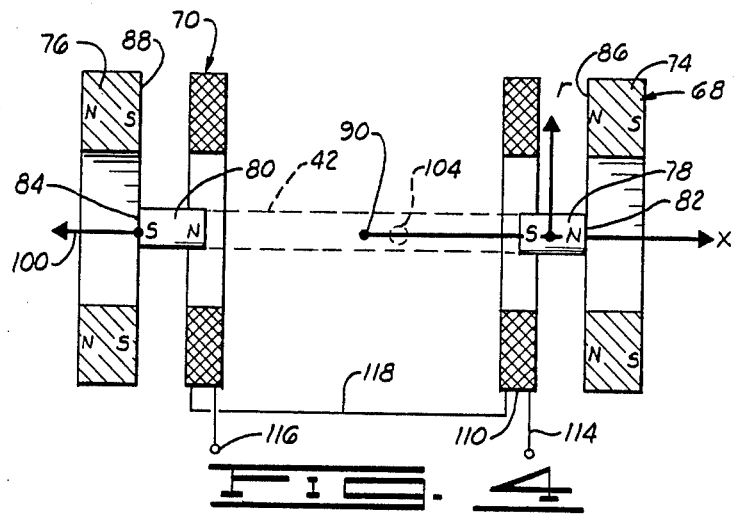
FIG. 4
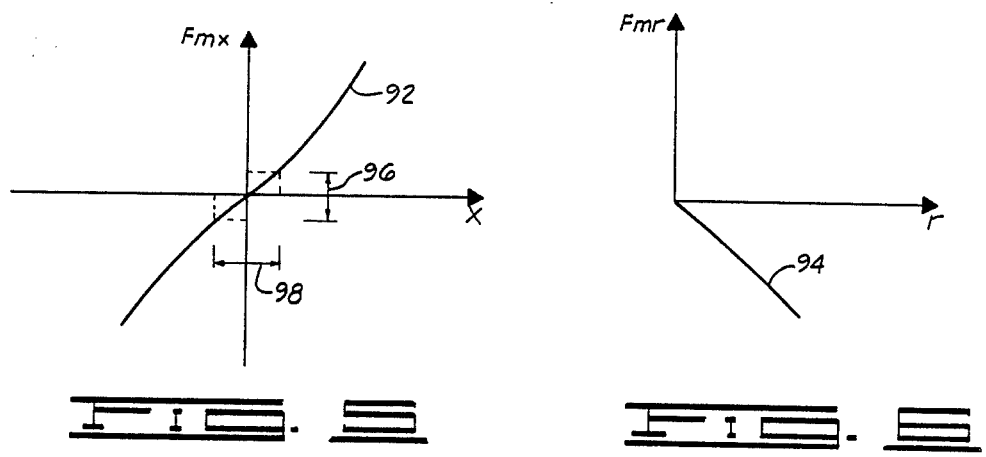
FIG. 5
FIG. 6
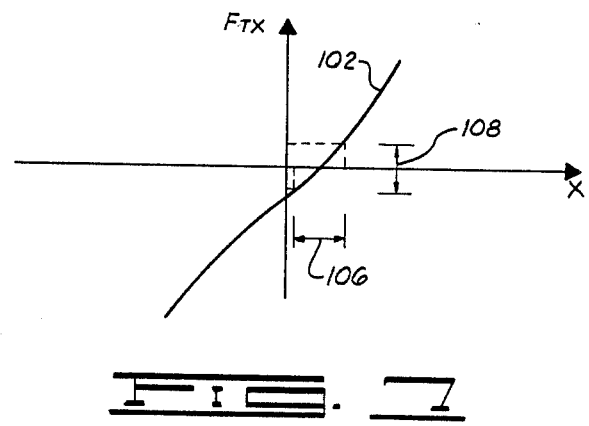
FIG. 7

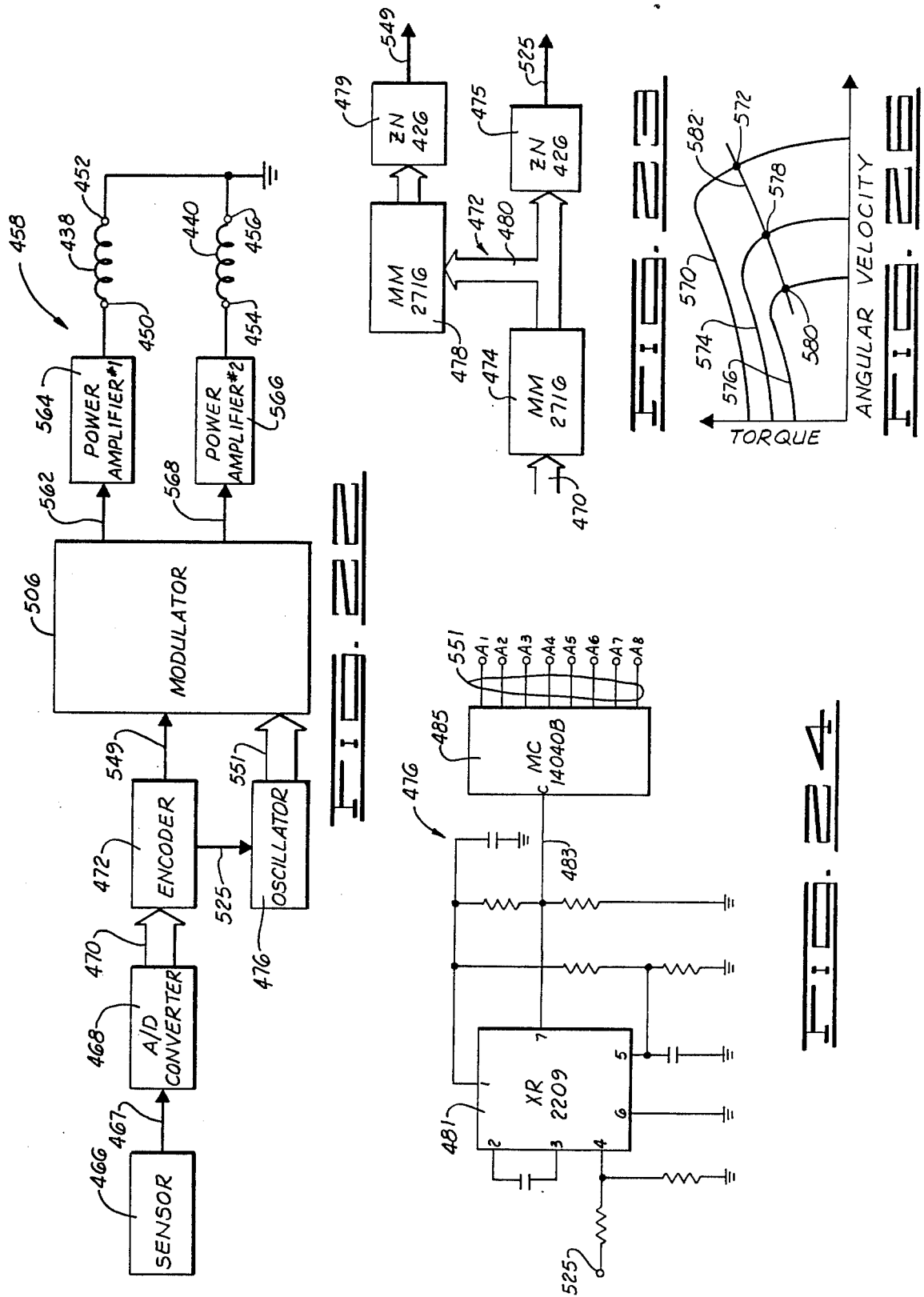

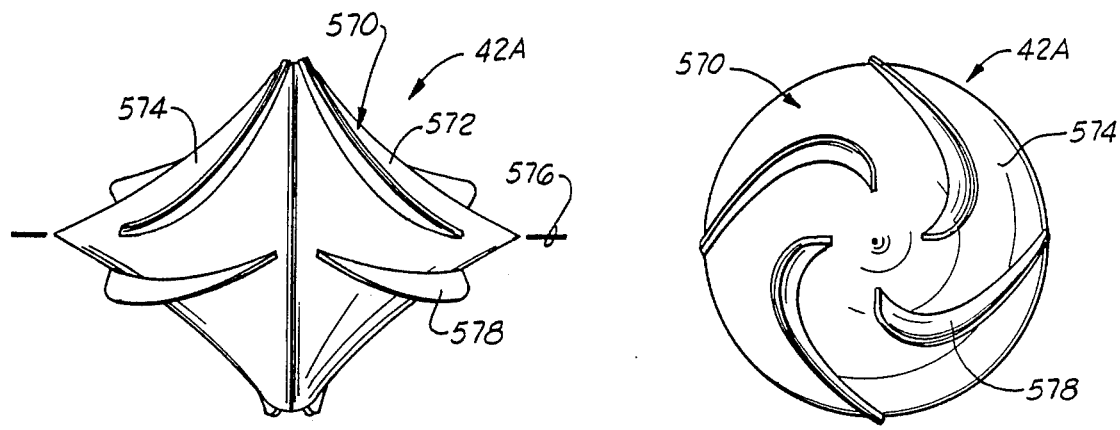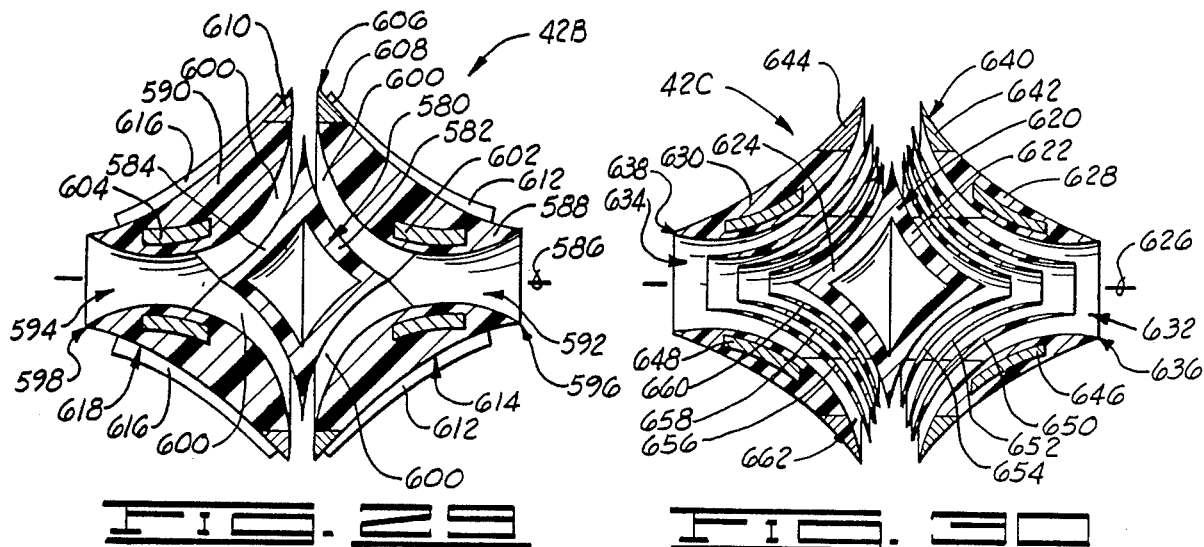

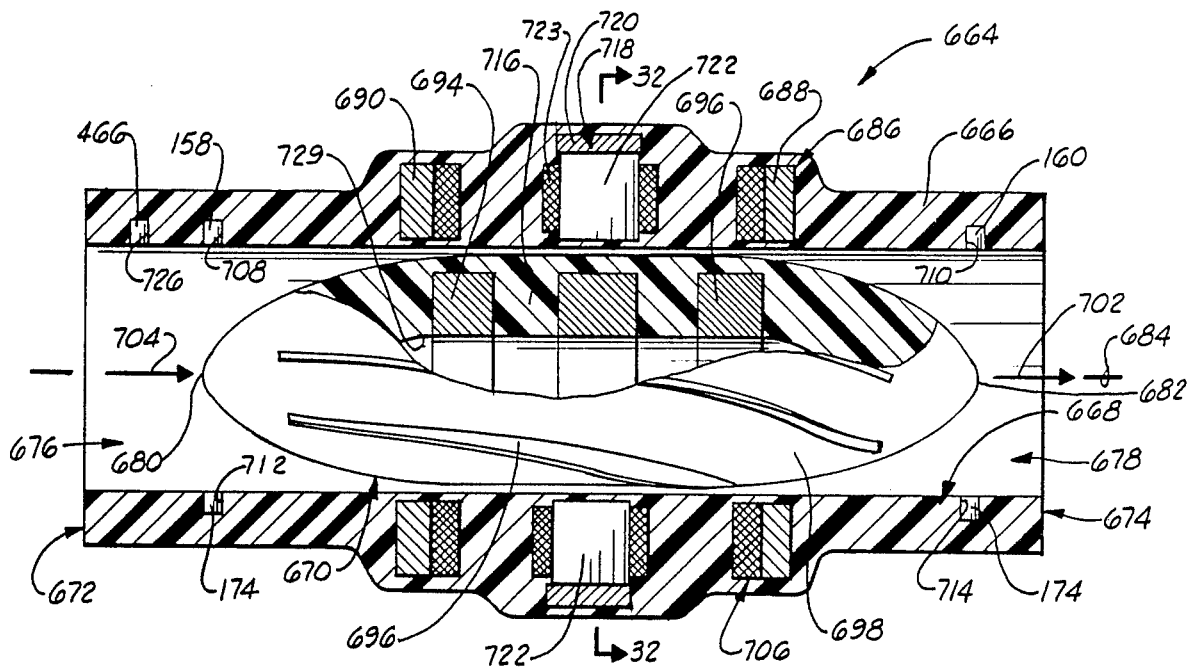
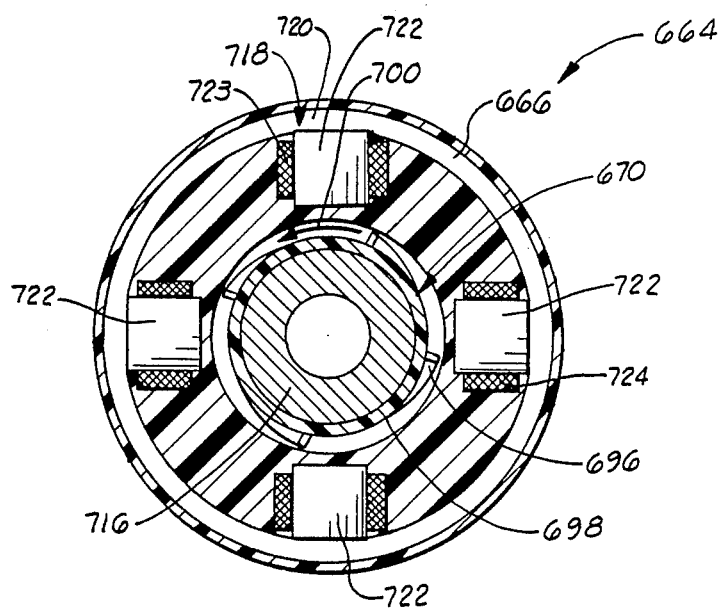

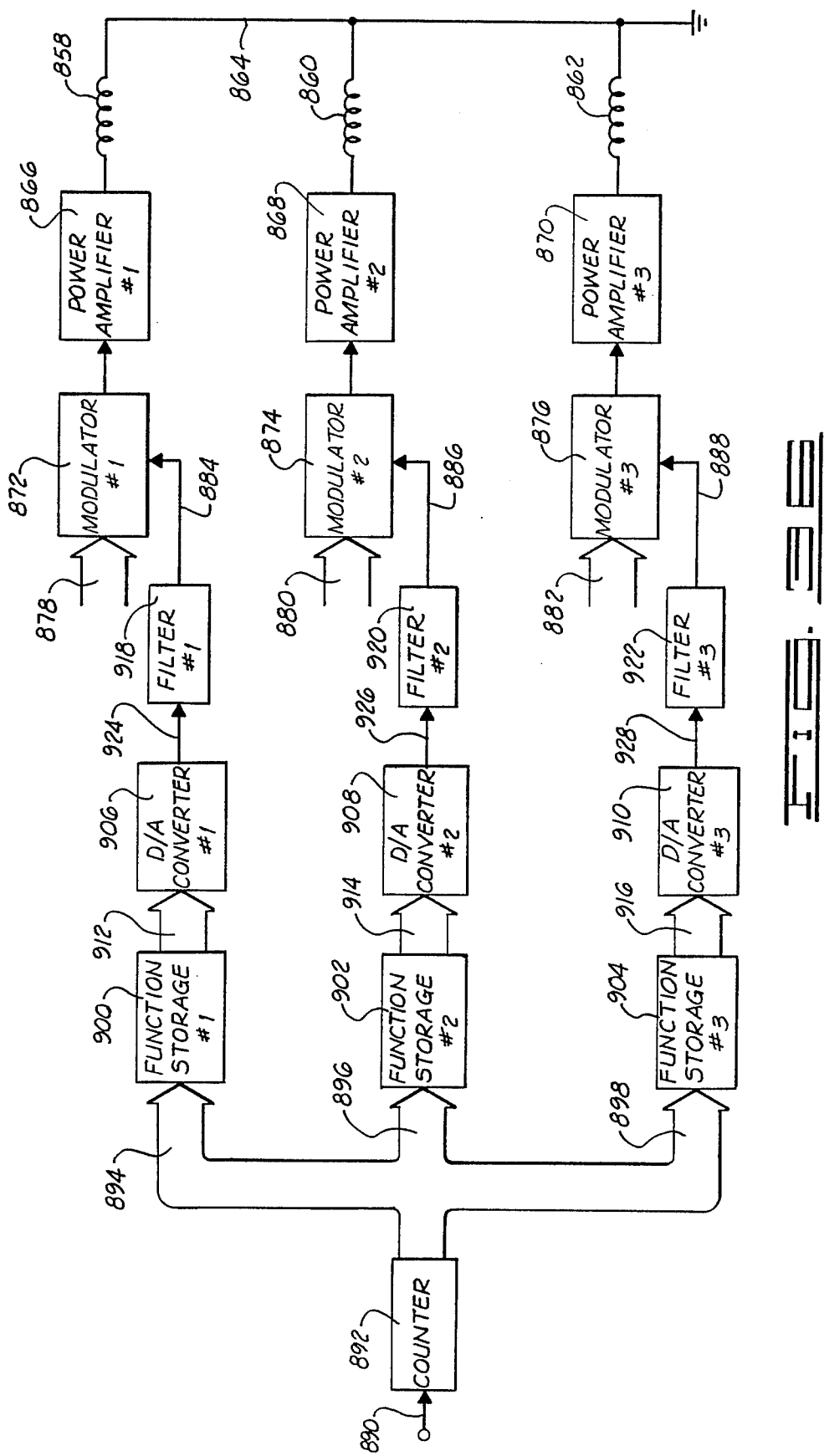

MAGNETICALLY SUSPENDED AND ROTATED ROTOR

This application is a continuation of Ser. No. 914,486, filed Oct. 2, 1986, entitled "MAGNETICALLY SUSPENDED AND ROTATED ROTOR" now abandoned, which is a continuation of Ser. No. 720,081, filed Apr. 4, 1985, entitled "MAGNETICALLY SUSPENDED AND ROTATED ROTOR" now abandoned.

BACKGROUND OF THE INVENTION

The present invention relates generally to apparatus for suspending and rotating rotors and, more particularly, but not by way of limitation, to the suspension and rotation of the impellors of pumps that can be implanted in the human body for replacing or assisting the natural heart in the pumping of blood through the circulatory system.

It has long been a goal of experimenters to develop a pump which can serve as an artificial heart and a variety of types of pumps have been designed to either replace or assist the natural heart in its function of pumping blood through the human body. While these prior art pumps have met with some degree of success, a number of problems associated with them have remained unsolved so that a practical artificial heart has not previously been developed. For a pump to be usable as a replacement or as an assist for the human heart, the pump must meet certain practical requirements which have been discussed in U.S. Pat. application Ser. No. 245,007, the teachings of which are hereby specifically incorporated herein by reference.

On a general level, the requirements for a blood pump are that it must not cause substantial injury to the blood and it must not require a large back-up system for its operation. Injury to the blood would preclude use of the pump over extended periods of time that would be required, for example, if the pump were to be a replacement for the natural heart or an assist that is to be implanted for the life of the patient. The size of the back-up system is a requirement that relates to the quality of life; for a pump to be practical, it must not require that the recipient be forever tied to an immobile life support system.

The requirement that the pump not require a large back-up system places certain technical requirements on the construction of a practical blood pump. One such requirement is that the pump be operable electrically so that the power supply for the pump can be provided by rechargeable batteries. At present, the technology is available to implant batteries within the human body and to recharge these batteries periodically using an induction coil that can be placed against the body as has been noted in the aforementioned U.S Pat. application Ser. No. 245,007. Similarly, it is presently possible to build highly efficient, electrically operated pumps in which the pumping action is achieved by the rotation of an impellor to cause a liquid to be driven through a chamber in which the impellor is located The problem that has not been solved prior to the present invention is to provide such a pump which will not cause unacceptable injury to blood.

A pump can injure blood in several ways. If the impellor of the pump is supported by mechanical bearings in contact with the blood, relative movement between parts of the bearings can result in excessive mechanical working of the blood causing blood cells to rupture Glands which might be used to seal these bearings cannot solve this problem. Since the impellor will be moving with respect to the gland, blood in the neighborhood of the gland-impellor interface will be subjected to high sheer stresses and friction which can cause the rupture of blood cells in much the same manner that rupturing of blood cells is occasioned in a bearing.

Another mechanical effect that can injure blood is the formation of regions within the pump in which the blood is stagnant or in which eddies without sufficient blood exchange, equivalent to stagnation, may occur. Stagnation tends to result in coagulation of the blood.

A third effect that can injure blood is excessive heating as the blood passes through the pump. If the pump is inefficient, so that a large part of the energy supplied to the pump appears as heat discharged into the blood, blood cells may be damaged through overheating or coagulation of the blood may occur. In this regard, it should be noted that albumen begins to denature at 42° C. so that inefficiency of the pump resulting in overheating of the blood can be a serious problem.

SUMMARY OF THE INVENTION

The present invention solves the problems that have been encountered with earlier blood pumps through a novel approach to rotor suspension and rotation, an approach which leads not only to a practical blood pump but additionally provides an apparatus which, it is contemplated, will have a variety of practical applications in a number of fields. Thus, the rotor can be the impellor of a pump and, more specifically, a blood pump that can be implanted in the body to replace or assist the natural heart. However, the invention is not limited to such use; rather, in its most general form, the invention is an apparatus for suspending and rotating a rotor for any useful purpose. For example, it is contemplated that the rotor might be the impellor of a pump that is used to pump radioactive, abrasive, or corrosive fluids, liquids containing dissolved gases, or the rotor of a gyroscope in a missile guidance system where power requirements play a role or any suspended rotor in an accelerated, moving system in general.

Nevertheless, it will be useful to consider the apparatus of the present invention in a specific context to fully bring out the benefits and advantages the invention provides. It is in this spirit of complete disclosure that the apparatus will be described with particular reference to the application in which the invention is particularly adapted to the pumping of blood through the human body.

As adapted for use as a blood pump, the apparatus of the present invention solves the problems that have been encountered with earlier blood pumps by providing a pump having an impellor that is magnetically suspended in a housing and magnetically rotated to effect the pumping of blood through the housing. Since the impellor is magnetically suspended and rotated, no bearings which might mechanically damage blood are needed in the pump and no bulky back-up system is needed to operate the pump. Rather, a battery pack can be utilized for this purpose. Moreover, the apparatus is constructed so that very little energy is expended in effecting the suspension of the impellor with the result that discharge of heat into the blood from the magnetic suspension system is held to a minimum level. An advantage of this construction is that the low power consumption needed to effect the suspension of the impellor enables a battery pack which can be used to operate the apparatus to be implanted in the body and periodically recharged as has been noted above. Thus, the present invention provides a heart replacement or assist that is capable not only of preserving the life of the user but one which will make that life meaningful by providing only minimal interference with the user's conduct of normal human affairs.

Additionally, the magnetic suspension of the impellor solves problems associated with pump lifetime. A severe problem that has been encountered with prior art pumps is wear and embrittlement of material of which the pumps are constructed and, in the case of blood pumps, wear and embrittlement of blood compatible materials that are included in the construction of the pumps. Both wear and embrittlement cause pump failure or changes in the surface structure of blood compatible materials, reducing the effectiveness of such materials, requiring termination of the use of the pump. The use of a magnetic bearing to support the impellor eliminates stresses that might otherwise be exerted on the materials, including blood compatible materials, of which the pump might be constructed. (A preferred construction of the pump of the present invention, when used as a blood pump, is the utilization of rigid substrates coated with a blood compatible material. An important advantage the magnetic suspension of the impellor of the present invention is that it permits all surfaces in contact with blood to be composed of materials which need not have special properties, such as flexibility, that are not associated with compatibility.) Thus, the magnetic suspension of the rotor eliminates bending stresses, frictional forces, and heating stresses to provide the pump with maintenance free, substantially indefinite lifetime.

To provide the pump adaptation of the apparatus with the capability of meeting these ends, the support of the impellor is effected by permanent magnets that are located on the impellor and the housing within which the impellor is rotated. Since the forces these magnets exert on the impellor to support it are conservative forces, the support of the impellor requires no expenditure of energy which might be degraded into heat and discharged into the blood to possibly cause injury to the blood. Rather, the only expenditure of energy required in the suspension of the impellor is energy used to stabilize the impellor suspension system and such energy expenditure can be minimized by supporting the impellor at a control position at which the impellor is in mechanical equilibruim.

It is well known that a suspension system comprised solely of permanent magnets cannot be stable so that no object can be supported solely by permanent magnets, a fact that is based on Earnshaw's theorem. However, the instability in the suspension of an object by permanent magnets is subject to control. That is, permanent magnets can be used to stably support an object with respect to some, but not all, degrees of freedom of movement of the suspended object about a selected support position and the degree of freedom for which the suspension is unstable can be selected. The present invention exploits this selection capability to provide a suspension system for a pump impellor that maximizes permanent magnet support forces while requiring very little energy to maintain the impellor in position in the pump housing, thereby minimizing the generation of heat by the suspension system to enable the pump to be used as a replacement for, or an assist to, the natural human heart in the pumping of blood through the circulatory system. Such power minimization also permits the use of much smaller components in a pump and the use of a highly portable power supply for the pump.

In the pump of the present invention, the permanent magnets are mounted on the pump impellor and on the pump housing and the magnetization of these permanent magnets is selected so that the permanent magnets will tend to align the rotation axis of the impellor with a selected support axis on the housing. With such selection, the permanent magnets will not stably support the impellor with respect to axial movement of the impellor along the housing support axis. Rather, the permanent magnets will tend to drive the impellor away from a null position on the housing support axis at which the permanent magnet forces cancel. An electromagnet is then provided, along with an electromagnet control circuit that controls the current through the electromagnet in accordance with impellor position, to exert axial forces on the pump impellor, via portions of the permanent magnet assembly mounted on the pump impellor, so that the electromagnet can be used to overcome the axial instability in the support of the impellor by the permanent magnet assembly. Since the electromagnet is used only to overcome the instability, as opposed to providing support for the impellor, very little power is required to operate the electromagnet. Moreover, and as practiced in one preferred embodiment of the invention, the current through the electromagnet can be continuously monitored and control of the current can be effected to maintain power consumption by the electromagnet at a minimum in the presence of static, or long term, axial forces on the impellor in addition to the forces arising from the permanent magnets and the electromagnet of the impellor suspension system. In the presence of static axial forces, the electromagnet drives the impellor toward a control position which is shifted slightly from the null position defined by the permanent magnets of the suspension system so that the static axial forces are balanced by a force provided by the permanent magnets of the suspension system. The invention thus provides, by way of example, flexibility in pump construction by enabling the permanent magnets of the suspension system to be used to counteract reaction forces on the impellor that occur as the result of pumping for certain pump designs.

In a pump constructed using the apparatus of the present invention, rotation of the impellor to pump blood is effected magnetically by constructing the pump impellor such that the impellor serves as the rotor of an electric motOr. In one preferred construction of the impellor, a shorting ring is formed about the periphery of the impellor and stator coils are mounted in the pump housing about the shorting ring so that the pump impellor is also the rotor of an eddy current induction motor. Thus, no mechanical connections need be made to the pump impellor to suspend and rotate the impellor so that construction of a blood pump following the teachings of the present invention eliminates any need for bearings, glands and the like in contact with blood which could cause mechanical damage to the blood. Additionally, the stator coils and shorting ring are placed in the pump so that the rotation of the impellor produces, at most, only negligible forces on the impellor that would have to be overcome by the magnetic suspension system of the impellor.

Another aspect of the present invention is the control of current through the stator coils that are provided to rotate the impellor of the pump. In the natural heart, a relationship known as the Frank-Starling effect exists between the flow rate of blood through the heart and the blood pressure at the inlet to the heart. The present invention contemplates the control of current supplied to the stator coils that, with the impellor, form an electric motor so that the pump of the present invention mimics the Frank-Starling effect of the natural heart. Such control can readily be adapted to provide for rotor speed control in accordance with a selected relationship to a selected measurable quantity in any application of the invention.

An important object of the present invention is to provide a rotor suspension and rotation apparatus which can be adapted to a variety of practical applications.

Another important object of the present invention is to provide a pump which can be implanted in the human body to provide a replacement for, or an assist to, the natural heart in the pumping of blood through the circulatory system.

Another object of the invention is to provide a blood pump which does not require a large back-up system that would interfere with the freedom of movement of a person in which the pump is implanted.

Another object of the invention is to provide a blood pump which is highly energy efficient so that damage to blood through discharge of heat into the blood is substantially eliminated.

Another object of the invention is to provide an energy efficient rotor suspension and control system that can be readily adapted to a variety of pump designs without loss of efficiency.

A further object of the invention is to provide an apparatus that eliminates the need for glands and bearings in pumps.

Another object of the invention is to provide a pump that avoids flexing and frictional engagement of moving parts.

Yet another object of the invention is to provide an apparatus for suspending and rotating a rotor in which the rotor speed can be controlled in accordance with the value of a selectable physical quantity.

Other objects, features and advantages of the present invention will become clear from the following detailed description of the invention when read in conjunction with the drawings and the appended claims.

BRIEF DESCRIPTION OF THE DRAWINGS

FIG. 1 is an isometric view of a pump, suitable for use as an implantable blood pump, constructed to employ the magnetic rotor suspension and rotation apparatus of the present invention.

FIG. 2 is a cross section of the pump shown in FIG. 1 taken along line 2—2 of FIG. 1.

FIG. 3 is a cross section of the pump shown in FIG. 1 taken along line 3—3 of FIG. 1.

FIG. 4 is a cross section of the magnets of the magnetic suspension system of the present invention illustrating the placement and magnetization of the permanent magnet assembly of the suspension system.

FIG. 5 is a graphical representation of the axial component of permanent magnet forces on the impellor of the pump shown in FIG. 1.

FIG. 6 is a graphical representation of the radial component of permanent magnet forces on the impellor of the pump shown in FIG. 1.

FIG. 7 is a graphical representation of the axial component of the total force on the impellor in the presence of a static, axial force on the impellor.

FIG. 19 is a graphical representation of the electrical characteristics of the power amplifier shown in FIG. 18.

FIG. 22 is a block circuit diagram of a rotation control circuit used to provide a current through the stator coils shown in FIG. 21.

FIG. 23 is a block diagram of the encoder of the rotation control circuit shown in FIG. 22.

FIG. 24 is a circuit diagram of the oscillator of the rotation control circuit shown in FIG. 22.

FIG. 26 is a graphical representation of an optimal operating characteristic of the impellor of the pump shown in FIG. 1.

FIG. 27 is a side elevational view of a modified impellor for the pump shown in FIG. 1.

FIG. 28 is an end elevational view of the impellor shown in FIG. 27.

FIG. 29 is a cross section in side elevation of another modification of the impellor of the pump shown in FIG. 1.

FIG. 30 is a cross section in side elevation of yet another modification of the impellor of the pump shown in FIG. 1.

FIG. 31 is a cross section in side elevation of a second embodiment of a pump employing the magnetic rotor suspension and rotation apparatus of the present invention.

FIG. 32 is a cross section of the pump shown in FIG. 31 along the line 31—31 of FIG. 31.

FIG. 36 is a block diagram of portions of the rotation control system of an apparatus, constructed in accordance with the present invention, having three stator coils to rotate a rotor.

DESCRIPTION OF FIGURES 1-26

Figure 8:
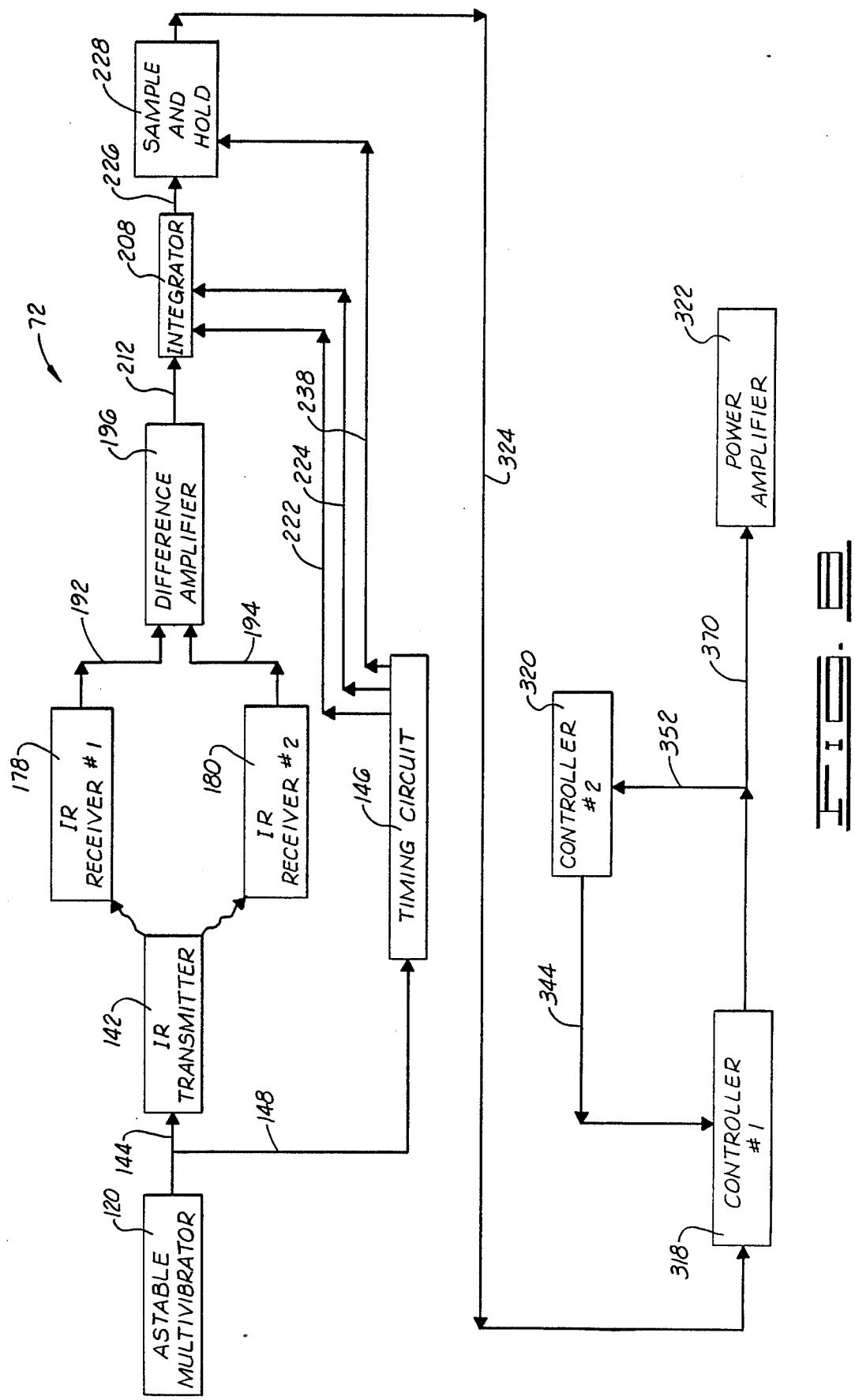
FIG. 8 is a block diagram of the electromagnet control circuit for the pump impellor.

Referring now to the drawings in general and to FIGS. 1-3 in particular, shown therein and designated by the general reference numeral 40 is an apparatus constructed in accordance with the present invention to include a magnetically suspended and rotated rotor. More specifically, the apparatus 40 is a centrifugal pump particularly suited for use as a blood pump that can be implanted in the human body to replace or assist the natural heart in the pumping of blood through the circulatory system and, at times, the apparatus 40 will, accordingly, be referred to as the pump 40. In this particular application of the apparatus 40, the rotor thereof, indicated at 42 in FIGS. 2 and 3, is configured to act as an impellor for the pump 40 and such rotor will, accordingly, also be referred to as the impellor 42.

The pump 40 is comprised of a housing 44 having a bore 46 formed therethrough about an impellor support axis 48 and central portions of the bore 46 are enlarged to form an impellor chamber 50 in which the impellor 42 is suspended as will be discussed below. Portions of the bore 46 to one side of the impellor chamber 50 form a first inlet passage 52 to the impellor chamber 50 and portions of the bore 46 of the other side of the impellor chamber 50 form a second inlet passage 54 to the impellor chamber 50. An outlet passage 56 is formed in central portions of the housing to extend tangentially from radially outermost portions of the impellor chamber 50 as shown in FIG. 3. An ever-widening groove 58 is formed in the housing 44 to extend circumferentially about the impellor chamber 50 to provide a smooth transition from the impellor chamber 50 to the outlet passage 56 and the impellor chamber 50 is formed by smoothly flared portions of the bore 46 to provide for laminar flow of blood from the inlet passages 52, 54 to the outlet passage 56, thereby preventing stagnation of blood in the pump 40 or the formation of closed eddies without blood exchange that could lead to coagulation of blood within the pump 50. Similarly, the housing 44 is constructed of, or coated with, a plastic, or other, material that is physically and chemically compatible with blood so that, with the smooth transitions from the inlet passages 52, 54 to the impellor chamber 50 and from the impellor chamber 50 to the outlet passage 56, no injury or blood damaging reaction will be occasioned to blood which might be pumped by the pump 40 arising from the contact between the blood and the interior of the housing 44.

The impellor 42 is similarly constructed of, or coated with, a rigid, blood-compatible material, e.g. plastic as shown, and is similarly shaped to provide for smooth flow of blood across the surface of the impellor 42. In particular, in the pump 40, the impellor 42 is rotated about an impellor rotation axis 60 which is maintained coincident with the support axis 48, in a manner to be discussed below, and the impellor 42 has two conical end portions, a first end portion 62 and a second end portion 64, having apices through which the rotation axis 60 extends. The bases of the portions 62 and 64, at which such portions are joined, are rounded as shown at 66 in FIG. 2 to provide for laminar flow of blood across the surface of the impellor 42.

The impellor 42 is positioned within the impellor chamber 50 by a magnetic suspension assembly (not numerically designated in the drawings) that is comprised of: a permanent magnet impellor support assembly 68, the form of which has been particularly illustrated in FIG. 4 (the permanent magnet impellor support assembly 68 will sometimes be referred to herein as a permanent magnet rotor support assembly consistently with other practical applications of the present invention that has been noted above); and an electromagnet 70; and an electromagnet control circuit 72 that has been particularly illustrated in FIG. 8.

Referring first to the permanent magnet impellor support assembly 68, such assembly is comprised of: a first housing magnet 74, having the form of a ring, that is mounted within the housing 44 to extend circumferentially about portions of the impellor chamber 50 adjacent the first inlet passage 52; a second housing magnet 76, similarly having the shape of a ring, that is mounted in the housing 44 to extend circumferentially about portions of the impellor chamber 50 adjacent the second inlet passage 54; a first impellor magnet 78, having the form of a cylinder, that is mounted within the impellor 42 to extend axially along the impellor rotation axis 60 near the apex of the first end portion 62 of the impellor 42; and a second impellor magnet 80, similarly having the form of a cylinder, that is mounted within the impellor 42 to extend axially along the impellor rotation axis 60 near the apex of the second end portion 64 of the impellor 42. Preferably, the magnets 74-80 are constructed of a cobalt-samarium alloy to provide the magnets 74-80 with a high retentivity that will result in large permanent magnet forces on the impellor 42 to support the impellor 42 within the impellor chamber 50.

The relative positions of the magnets 74-80 and the directions in which the magnets 74-80 are magnetized are selected, in a manner that has been indicated in FIG. 4, to provide a permanent magnet force profile on the impellor 42 that has been graphically illustrated in FIGS. 5 and 6. (FIG. 4 has been drawn for the preferred case, achievable by selection of the magnets 74-80, in which the magnets 74-80 are homogeneously magnetized so that their magnetic axes coincide with their geometric axes.) In particular, and as shown in FIG. 4, the magnets 74-80 are axially magnetized in the same direction so that magnetic poles indicated in FIG. 4 appear at the radially extending faces of the housing magnets 74, 76 and at the ends of the impellor magnets 78, 80. The separation of the housing magnets 74, 76 is selected with respect to the separation of the impellor magnets 78, 80 so that, when the impellor 42 (schematically indicated in FIG. 4 by dashed lines connecting the impellor magnets 78, 80 and numerically indicated by the numerical indication 42 for the impellor 42) is axially centered in the impellor chamber 50, the outside ends 82 and 84 of the impellor magnets 78 and 80 respectively will be in axial alignment with the inside faces 86 and 88 of the housing magnets 74 and 76 respectively. Thus, a north pole on one of the impellor magnets 78, 80 will be surrounded by a north pole of one of the housing magents 74, 76 and a south pole on the other of the impellor magnets 78, 80 will be surrounded by a south pole on the other of the housing magnets 74, 76.

With the magnets 74–76 so magnetized and positioned, axial forces that the permanent magnet support assembly 68 exerts on the impellor 42, via the mounting of the impellor magnets 78, 80 thereon, will cancel when the impellor 42 is axially centered in the impellor chamber 50 to define a null position of the impellor 42 in the housing 44. Such position is indicated in FIG. 4 as a point 90, representing the geometric center of the impellor magnet 78 and 80, located at the geometric center of the housing magnets 74 and 76 at which the geometric center of the impellor magnets 78, 80 will be located when the impellor 42 is centered in the impellor chamber 50. (The geometric center of magnets 78, 80 is located at the geometric center of the impellor 42 for a reason to be discussed below.) Should the impellor 42 be axially shifted away from the null position; that is, should the geometric center of the impellor magnets 78, 80 move away from the point 90 along the x axis indicated in FIG. 4, such axis coinciding with the housing support axis 48 in FIG. 2, the axial force on the impellor 42 will have the form of the curve 92 shown in FIG. 5 which is a graph of the axial component of the permanent magnetic force (plotted as the ordinate) versus the position of the impellor along the housing support axis 48 (plotted as the abscissa) with the origin of the graph corresponding to location of the impellor 42 at the null position. As shown in such Figure, should the center of the impellor 42 move from the point 90 in the direction of increasing x (to the right in FIG. 4), the axial component, $F_{mx}$, of the permanent magnet force on the impellor will have a positive value; that is the axial component of the permanent magnet force on the impellor will also be to the right in FIG. 4. Conversely, should the impellor move to the left of the null position indicated in FIG. 4, the axial component of the permanent magnet force on the impellor 42 will also be to the left as indicated by negative values of the axial component force curve 92 in FIG. 5. Thus, the permanent magnet impellor support assembly 68 exerts no axial force on the impellor 42 at such times that the impellor 42 is in the null position in which the geometric center of the impellor magnets 78, 80 is coincident with the geometric center of the housing magnets 74 and 76 and exerts an axial force on the impellor 42 tending to drive the impellor 42 away from the null position at such times that the impellor is axially displaced from the null position so that the null position is a position of unstable equilibrium with respect to an axial degree of freedom of the impellor 42 in the housing 44.

However, with respect to radial movement of the impellor 42, the null position 90 is a position of stable equilibrium for the impellor 42 and, moreover, the position of the impellor 42 in which the rotation axis 60 parallels the support axis 48 is a position of stable equilibrium for angular degrees of freedom of the impellor about any axis perpendicular to the x axis of FIG. 4. (Because of the cylindrical symmetry of the permanent magnet impellor support assembly 68, the permanent magnets 74–80 exert essentially no torque about the x axis on the impellor 42 for any position of the impellor 42 in the impellor chamber 50.) The radial and angular stability of the impellor 42 can be seen from a graph of the radial component of the permanent magnet force on one of the impellor magnets 78–80 versus displacement of the magnet from the x axis in FIG. 4; that is, a graph of the radial force on the magnet as a function of a coordinate r shown in FIG. 4. (Because of the cylindrical symmetry of the magnets 74–80, the coordinate r can extend in any direction from the x axis.) Such a graph has been included for the impellor magnet 78 as FIG. 6 in which the radial component of the permanent magnet force on the impellor magnet 78 has been plotted on the ordinate of the graph in FIG. 6 and the radial displacement of the magnet 78 has been plotted along the abscissa. With the permanent magnets 74–80 magnetized and relatively positioned as shown in FIG. 4, the radial component, $F_{mr}$, of the permanent magnet force on the impellor magnet 78 has the general form of the curve 94 in which such component is negative for all positive values of the variable r that indicates displacement of the axis of the magnet 78 from the x axis. That is, should the magnet 78 become displaced radially from the axis x, which lies along the housing support axis, the housing magnets will exert a force on the impellor magnet 78 that tends to return the impellor magnet 78 to the x axis. Similarly, the housing magnets will tend to maintain the axis of the impellor magnet 80 on the housing support axis so that any misalignment of the impellor rotation axis, along which the impellor magnets 78 and 80 extend, with the housing support axis, along which the x axis extends, will result in permanent magnet forces on the impellor 42 that will tend to realign the impellor rotation axis 60 with the housing support axis 48. Because of the repulsion that exists between the magnets 74 and 78 and between the magnets 76 and 80, such repulsion arising from the juxtaposition of like magnetic poles of the housing and impellor magnets, and the axial magnetization of the magnets 74–80, large changes in the magnetic field about the magnets 74–80 will occur for small misalignments of the axes 48 and 60. Thus, the forces tending to align the axis 48 and 60 will be sufficiently strong to very stably support the impellor 42 with respect to the coincidence of the axes 48 and 60.

It will thus be seen that the permanent magnet impellor support assembly 68 exerts forces on the impellor 42 which tend to align the rotation axis 60 of the impellor 42 with the housing support axis 48 while tending to drive the impellor 42 axially away from the null position in which the geometric center of the impellor 42 is located at the point 90 in FIG. 4 at such times that the impellor is displaced axially away from the null position. Moreover, in the absence of additional static axial forces on the impellor 42, only a small control force, which is supplied by the electromagnet 70 in a manner to be discussed below, is needed to keep the impellor at the null position as can be seen from the graph of FIG. 5. To maintain the impellor 42 at the null position, the control force need only be sufficient to overcome the axial component of the permanent magnet force on the impellor and such axial component is small so long as the impellor 42 is near the null position as has been shown by the range 96 of the axial component of the permanent magnet force on the impellor 42 corresponding to a small range 98 of position of the impellor 42 about the null position in FIG. 5.

FIG. 5 has been drawn for the case in which the only axial force on the impellor 42, other than the control force exerted thereon by the electromagnet 70, is the force exerted on the impellor 42 by the permanent magnet impellor support assembly 68. In this case, the null position 90 is also a position of mechanical equilibrium of the impellor 42 and it is the fact that the position is one of mechanical equilibrium that limits the force the electromagnet 70 must exert on the impellor magnets 78, 80 to stabilize the impellor 42 in the impellor chamber 50. The present invention contemplates the exploitation of this characteristic of stabilization about an equilibrium position, as well as the general form of the axial component of the permanent magnet force on the impellor 42, to cause the permanent magnets 74–80 to support the impellor 42 against additional axial forces that might be exerted on the impellor 42; for example, reaction forces on the impellor 42 which might arise from an imbalance in the supply of blood to the two inlet passages 52 and 54 of the pump housing 44. Thus, no additional energy to support the impellor 42 will be supplied to the electromagnet 70 to support the impellor 42 in the impellor chamber 50 beyond the small energy requirements necessary for stabilization of the impellor 42. The manner in which the permanent magnets 74–80 are caused to support the impellor 42 in the presence of an additional static axial force has been illustrated in FIGS. 4 and 7.

In FIG. 4, an additional static force on the impellor 42 has been indicated at 100 by an arrow that, for purposes of illustration, has been drawn to the left in FIG. 4 so that the force 100 is in the negative x direction in such Figure. In the presence of the force 100, the axial component of the total force, $F_{TX}$, on the impellor, excluding the control force exerted on the impellor by the electromagnet 70, as a function of impellor position has the form of the curve 102 which differs from the curve 92 in FIG. 5 in that the curve 102 is shifted downwardly along the force axis from the position of the curve 92 in FIG. 5. In this case, the null position for the impellor 42 (the origin of coordinates in FIG. 7) is not a position of equilibrium for the impellor 42; rather, the position of mechanical equilibrium for the impellor 42 occurs for a small positive value of the axial coordinate x corresponding to the location of the center of the impellor 42 at the position, relative to the housing magnets 74 and 76, indicated by the dashed circle 104 in FIG. 4. Such position will be referred to herein as a control position of the rotor and, as will be discussed below, the electromagnet control circuit 72 is constructed to pass currents through the electromagnet 70 to drive the impellor 42 toward the control position 104 at such time that the impellor 42 is displaced from the control position 104. Thus, a range of positions of the impellor 42 about the control position 104 at which the electromagnet 70 stabilizes the impellor 42 corresponds to only a small range 108 in a control force the electromagnet 70 must exert on the impellor magnets 78, 80 to stabilize the position of the impellor 42 in the impellor chamber 50. As can be seen in FIG. 4, the control position is shifted from the null position in a direction opposite the direction in which the force 100 is exerted on the impellor 42. In the special case in which the additional axial force 100 is non-existent, the control position 104 is coincident with the null position 90.

A suitable form of construction for the electromagnet 70 has also been illustrated in FIG. 4; that is, the electromagnet 70 is comprised of a flat, toroidal coil 110 positioned coaxially with the housing magnets 74, 76 and in abutment with the inside face 86 of the magnet 74 and a flat, toroidal coil 112 similarly positioned coaxially with the magnets 74, 76 and in abutment with the inside face 88 of the magnet 76 so that the windings of the coils 110, 112 extend circularly about portions of the impellor magnets 78 and 80 adjacent the ends 82 and 84 of the magnets 78 and 80 respectively. The coils 110, 112 can be connected either serially or in parallel and the serial connection has been shown in FIG. 4 for purposes of illustration. In such connection, the electromagnet 70 has two input terminals 114 and 116, each providing an electrical connection to one of the coils 110, 112, and a conductor 118 connects the two coils 110, 112 together In making such connection and providing such inputs to the coils 110, 112, it is important to observe a polarity relationship between the two coils 110, 112 that has been indicated for the serial connection by the locations of the input terminals 114, 116 at the right hand sides of each of the two coils 110, 112 in FIG. 4. Specifically, the two coils 110, 112 are connected together or, in the case of parallel connection, are connected to the electromagnet control circuit so that currents passed through the two coils will produce a magnetic field in one direction through the center of one coil 110, 112 and will produce a magnetic field in the opposite direction through the center of the other coil 110, 112. With the magnetizations of the impellor magnets 78, 80 that has been shown in FIG. 4, the opposite directions of the magnetic fields produced by passing a current through the coils 110, 112 results in the force that one coil exerts on the impellor magnet partially disposed within such coil being in the same direction as the force the other coil exerts on the other impellor magnet.

For purposes which will be discussed below, it is desirable that the impellor 42 be light in weight and the use of two impellor magnets 78, 80 in the impellor 42, rather than one impellor magnet that extends nearly the length of the impellor 42, is utilized to limit the weight of the impellor 42. However, the use of two impellor magnets will also result in a geometrical limitation of the force that the magnetic field produced by each coil of the electromagnet 70 produces on the impellor magnet about which the coil extends, such limitation arising from the presence of opposite magnetic poles at the two ends of each of the impellor magnets. It has been found that a suitable construction of the coils of the electromagnet 70 and the impellor magnets 78, 80 that will provide efficient operation of the magnetic suspension assembly despite this force limitation is the construction of the impellor magnets 78 and 80 to have lengths approximately equal to the axial extents of the magnets 74 and 76 with the magnets 78 and 80 extending into the coils 110 and 112 of the electromagnet for approximately one-third the axial extent of the coils 110 and 112 as shown in FIG. 4. (The magnet geometry has been schematized in remaining Figures to simplify illustration of the present invention. The preferred geometry is that shown in FIG. 4.) The radial extents of the coils 110, 112 of the electromagnet can be varied to adjust the relationship between the current through the electromagnet 70 and the axial force exerted on the impellor 42 by the electromagnet 70. Thus, the coils 110, 112 of the electromagnet 70 can be provided with a larger outside radius than the outside radius of the housing magnets 74 and 76 as has been shown in FIG. 2. Similarly, the inside radii of the coils 110, 112 need not be the same as the inside radii of the housing magnets 74, 76 but can be larger to accommodate the flaring of the bore 46 through the housing 44 to form the impellor chamber 50 as has also been indicated in FIG. 2.

Coming now to the electromagnet control circuit 72, shown in FIG. 8, it should first be noted that the circuit 72 makes extensive use of integrated circuits to limit both the physical size of the electronics package of the apparatus 40 and the cost of manufacturing such package. Moreover, to insure reliability of the circuit 72, use has been made, where appropriate, of standard circuits which each carry out a specific function in the overall circuit 72 so that the novel aspects of the electromagnet control circuit 72 lie in selection and combination of the specific functional circuits of which the electromagnet control circuit 72 is comprised to provide the circuit 72 with an overall, novel scheme of operation. In order to stress these novel aspects of the electromagnet control circuit 72, individual circuits which comprise the circuit 72 will be only briefly discussed to indicate components which can suitably be used in these circuits. In keeping with this stress on the electromagnet control circuit 72 as a whole, power and ground connections to the integrated circuits which are specified in manufacturer's literature for the circuits have not been illustrated in the drawings except in those instances in which it is useful to do so to bring out a feature that contributes to the operation of the circuit 72 as a whole. Similarly, the power supply for the circuit 72 has not been illustrated. It is contemplated that such power supply is a battery pack that can be recharged using a conventional recharging circuit that can be implanted in the human body and inductively coupled to a charging coil positionable against the body as discussed in the aforementioned U.S. Pat. application Ser. No. 245,007. Since the requirements for the battery pack are imposed by the requirements of standard electrical components that are described in the manufacturer's literature for such components, the illustration of the battery pack and connections between components of the circuit 72 and the battery pack would serve only to complicate the drawings so that, in the interest of clarity of description, the battery pack and connections thereto have not been illustrated. It is to be understood that the circuit 72 has a common ground which is taken at a connection between two batteries of the battery pack so that a variety of positive and negative voltages can be supplied to components of the circuit 72 to provide electrical power to such components in accordance with needs specified in manufacturer's literature for such components.

Figure 9:
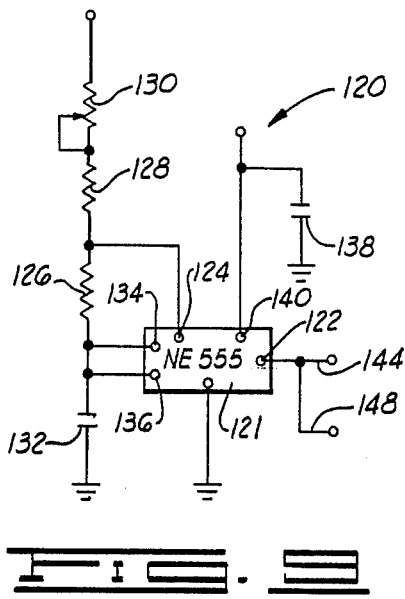
FIG. 9 is the circuit diagram of the astable multivibrator of the electromagnet control circuit.

Referring now to FIG. 8, the electromagnet control circuit 72 comprises an astable multivibrator 120 which has been more particularly illustrated in FIG. 9. The multivibrator 120 is of conventional construction that employs a type 555 timer 121 and a plurality of resistors and capacitors connected thereto to provide a square wave signal at the timer output terminal 122 which serves as the output terminal of the multivibrator 120.

In the blood pump adaptation of the invention, a suitable frequency for the square wave signal produced by the astable multivibrator 120 is 40 kilohertz which, as will become clear below, results in a sampling time for repositioning the impellor 42 of approximately 0.15 milliseconds. Such sampling time is short enough to provide effective control of the position of the impellor 42 in the impellor chamber 50 and long enough to ensure high efficiency of light emitting diodes used in the electromagnet control circuit 72 as will be discussed below. To achieve the 40 kilohertz operating frequency, the discharge terminal 124 of the timer is connected between fixed 1.8 kilohm and 8.2 kilohm resistors, 126 and 128 respectively, the 8.2 kilohm resistor 128 is connected to the power supply via a 2.8 kilohm variable resistor 130, the 1.8 kilohm resistor is connected via a 2.2 nanofarad capacitor to the circuit ground, and the trigger and threshold terminals, 134 and 136 respectively of the timer 121 are connected between the 1.8 kilohm resistor 126 and the capacitor 132. A 220 microfarad capacitor 138 is connected between the power terminal 140 of the timer 121 and the circuit ground to provide a short circuit for transients that might otherwise be transmitted to other components of the electromagnet control circuit 72 via the power supply as is known in the art.

Figure 10:
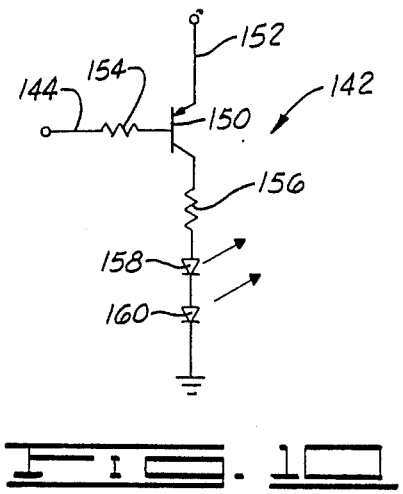
FIG. 10 is the circuit diagram of the IR transmitter of the electromagnet control circuit.

The square wave signal generated by the astable multivibrator 120 is applied to an infrared transmitter 142 that has been particularly illustrated in FIG. 10 via a conductor 144 and to a timing circuit 146 that will be discussed below via a conductor 148. Referring to FIG. 10, the infrared transmitter comprises a pnp transistor 150 which, in the blood pump application of the present invention can suitably be a type BC 161 transistor. The emitter of the transistor 150 is connected to the power supply via a conductor 152 and the base of the transistor 150 is connected to the output terminal 122 of the timer 121 via the conductor 144 and a resistor 154 which, in the blood pump application of the invention, has a resistance of 5.6 kilohms. The collector of the transistor 150 is connected to the circuit ground via a 56 ohm resistor 156, a first light emitting diode 158, and a second light emitting diode 160. The light emitting diodes 158 and 160 are selected to produce bursts of infrared radiation when the diodes are pulsed and suitable light emitting diodes for use in the infrared transmitter 142 are type SFH 400 light emitting diodes.

The positioning of the diodes 158 and 160 in the pump 40 has been illustrated in FIG. 2 to which attention is invited. A socket 162 is formed in the wall of the first inlet passage to receive the light emitting diode 158 and the socket 162 is positioned and oriented so that the beam of infrared radiation produced by the light emitting diode 158 is directed diametrically across the inlet passage 52 and such that the center of the beam is aligned with one end 164 of the impellor 42 when the impellor 42 is disposed in the null position thereof. Thus, the beam of infrared radiation produced by the diode 158 is partially blocked by the impellor 42 and the degree to which such beam of radiation is blocked depends upon the position of the impellor 42 in the impellor chamber 50. Similarly, a socket 166 is formed in the wall of the second inlet passage 54 to receive the light emitting diode 160 and the socket 166 is positioned and oriented with respect to the opposite end 168 of the impellor 42 in the same manner that the socket 162 is positioned and oriented with respect to the end 164 of the impellor 42. Diametrically opposed to the sockets 162 and 166, sockets 170 and 172 respectively are formed in the walls of the passages 52 and 54 to receive phototransistors 174 and 176 which are part of first and second infrared receivers 178 and 180 respectively shown in FIG. 8.

Figure 11:
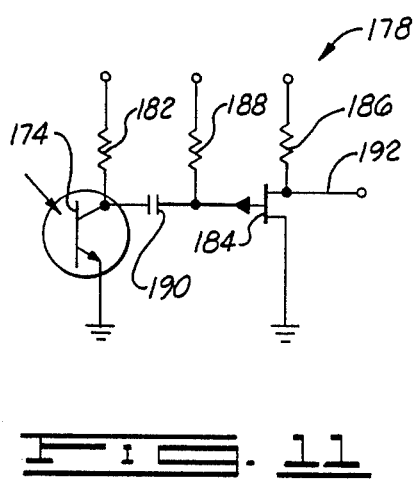
FIG. 11 is the circuit diagram of one of the IR receivers of the electromagnet control circuit.

The infrared receivers 178 and 180 are identical in construction and such construction has been shown for the first infrared receiver 178 in FIG. 11. In particular, the first infrared receiver 178 is comprised of two capacitively coupled amplifiers, one of which includes the phototransistor 174. The phototransistor 174 is preferably a type BPY 61/II phototransistor having an emitter connected to the circuit ground and a collector connected to the power supply via a 5.6 kilohm resistor 182. The second amplifier of the first receiver 178 is comprised of a type 2N3819 p channel field effect transistor 184 having a drain connected to the system ground and a source connected, via a 2.7 kilohm resistor to the circuit power supply. A 100 kilohm resistor 188 provides a bias to the gate of the transistor 184 and the two amplifiers of the infrared receiver 178 are coupled via a 10 nanofarad capacitor 190 that is connected between the collector of the phototransistor 174 and the gate of the field effect transistor 184. The output of the first infrared receiver 178 is supplied on a conductor 192 connected to the source of the field effect transistor 184 and the output of the second infrared receiver 180 is similarly supplied on a conductor 194 as shown in FIG. 8.

The construction of the infrared receivers 178, 180 as two capacitively coupled amplifiers serves to prevent ambient light from interfering with the control of the stablization of the impellor 42. That is, ambient light to which the pump 40 might be subjected would give rise to a DC component in the output of the phototransistor 174 that would be blocked by the coupling capacitor 190 so that the signals appearing on the conductors 192 and 194 of the first and second infrared receivers respectively are related solely to the illumination of the phototransistors 174 and 176 by the light emitting diodes 158 and 160. Use of field effect transistors in the infrared receivers serves to provide an impedance match between the phototransistors 174, 176 and a difference amplifier 196 which receives the outputs of the infrared receivers 178, 180 as shown in FIG. 8.

Figure 12:
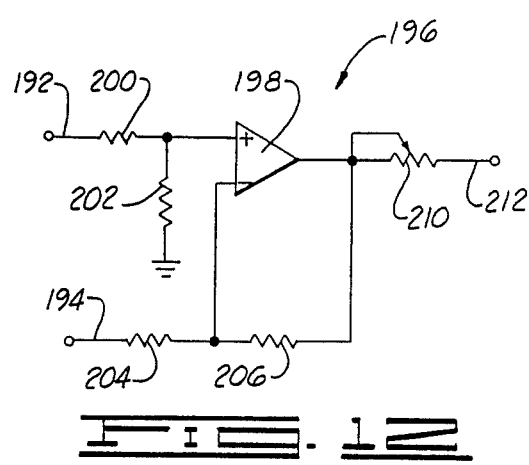
FIG. 12 is the circuit diagram of the difference amplifier of the electromagnet control circuit.

The construction of the difference amplifier 196 has been particularly shown in FIG. 12. As illustrated therein, the difference amplifier 196 comprises an operational amplifier 198 which is preferably one of four operational amplifiers included in a type TL084 integrated circuit The non-inverting input of the operational amplifier 198 is connected to the output of the first infrared receiver 178 via the conductor 192 and a 100 kilohm resistor 200 and to the circuit ground via a 100 kilohm resistor 202. The inverting input of the operational amplifier 198 is connected to the output of the second infrared receiver 180 via the conductor 194 and a 100 kilohm resistor 204 and is further connected to the output of the operational amplifier 198 via a 100 kilohm resistor 206. Thus, the output of the operational amplifier 198 is a signal that is proportional to the difference in the two signals received on the conductors 192 and 194 from the two infrared receivers 178 and 180. Such output, which can be positive or negative with respect to the circuit ground depending upon the location of the impellor 42 with respect to the null position thereof, is provided to an integrator 208 via a variable 100 kilohm resistor 210 and a conductor 212.

Figure 13:
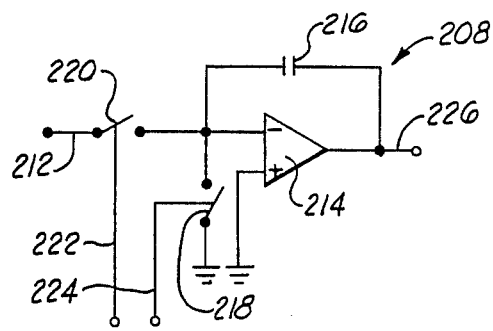
FIG. 13 is a circuit diagram for the integrator of the electromagnet control circuit.

The integrator 208, which has been particularly illustrated in FIG. 13, is comprised of an operational amplifier 214, which is a second of the operational amplifiers of the above-mentioned TL084 integrated circuit, and a 10 nanofarad capacitor 216 that is connected between the output of the operational amplifer 214 and the inverting input thereof so that the capacitor 216 will store a charge in response to a signal supplied to the inverting input of the operational amplifier 214, such charge being proportional to the integral of the signal supplied to such input Integrated circuit switches 218 and 220 connect the inverting input of the operational amplifier 214 to the circuit ground and to the conductor 212 from the difference amplifier 196 respectively so that the integrator 208 can be periodically reset, by closing the switch 218 to discharge the capacitor 216, and subsequently connected to the output of the difference amplifier 196 by closing the switch 220. Subsequent to the closure of the switch 220, a charge that is proportional to the integral of the difference amplifier output following reset of the integrator 208 will accumulate on the capacitor 216 in a conventional manner. Suitable switches for resetting the integrator 208 and subsequently connecting the integrator 208 to the difference amplifier 196 are provided by the HI-201 integrated circuit which includes four single pole single throw CMOS analog switches that open in response to an electrical signal and are otherwise closed. In particular, the switch 220 can be opened via a signal supplied on a conducting path 222 and the switch 218 can be opened by an electrical signal supplied on the conducting path 224 shown in FIG. 13, such paths leading to the timing circuit 146 that has been illustrated in FIG. 15.

Figure 14:
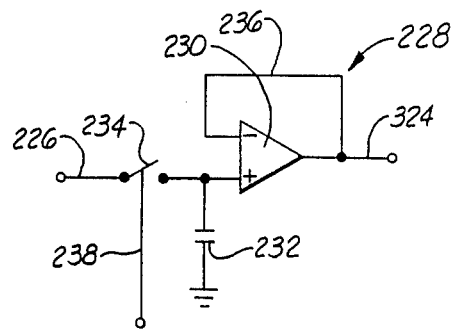
FIG. 14 is a circuit diagram of the sample and hold of the electromagnet control circuit.

The output of the operational amplifier 214 of the integrator 208 is connected, via a conductor 226, to a sample and hold circuit 228 that is constructed as shown in FIG. 14. The sample and hold circuit 228 is comprised of an operational amplifier 230 having a non-inverting input connected, via a 10 nanofarad capacitor 232, to the circuit ground and, via an integrated circuit switch 234, to the conductor 226 from the integrator 208 The output of the operational amplifier 230 is fed back to the inverting input of the operational amplifier 230 via a conductor 236 so that the output of the operational amplifier 230 will be proportional to a charge stored on the capacitor 232 The operational amplifier 230 is conveniently another one of the four operational amplifiers constructed on the previously mentioned 15 TL084 integrated circuit and the switch 234 is similarly another one of the switches on the previously mentioned HI-201 integrated circuit Like the switches 218 and 220, the switch 234 is open at such times that an electrical signal is received thereby on a conductor 236 from the timing circuit 146 and is closed in the absence of such a signal.

The timing circuit 146 is constructed to count pulses produced by the astable multivibrator 120 and control the integrator 208 and sample and hold circuit 228 so that the integrator 208 periodically accumulates a charge proportional to the displacement of the impellor 42 from the null position thereof for a selected number of pulses produced by the astable multivibrator 120 after which a portion of the charge is transferred to the sample and hold circuit 228 while the integrator 208 is reset for the accumulation of a new charge. The current through the electromagnet 70 is continuously controlled, as will be discussed below, in relation to the charge stored in the sample and hold circuit 228 so that the periodic accumulation of a charge determinative of the location of the impellor 42 and periodic transfer of such charge to the sample and hold circuit 228 can be used to cause the electromagnet 70 to exert forces on the impellor 42 that will stabilize the axial position of the impellor 42 in the impellor chamber 50.

Figure 15:
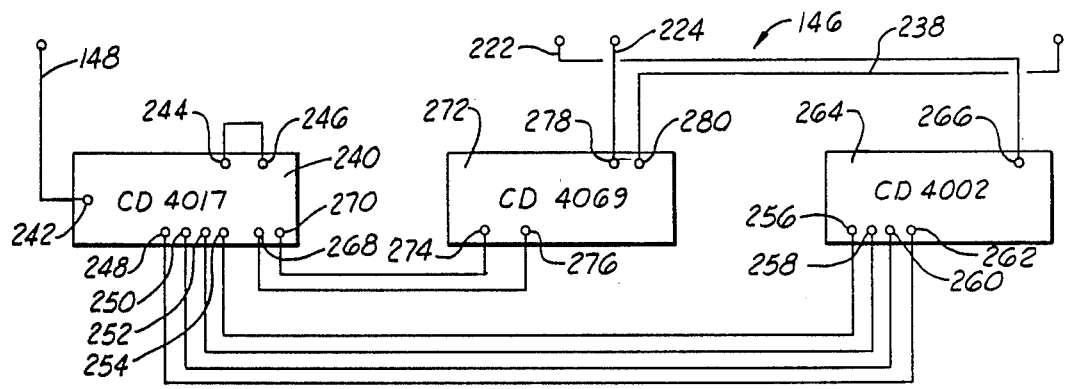
FIG. 15 is a circuit diagram of the timing circuit of the electromagnet control circuit.
Figure 20:
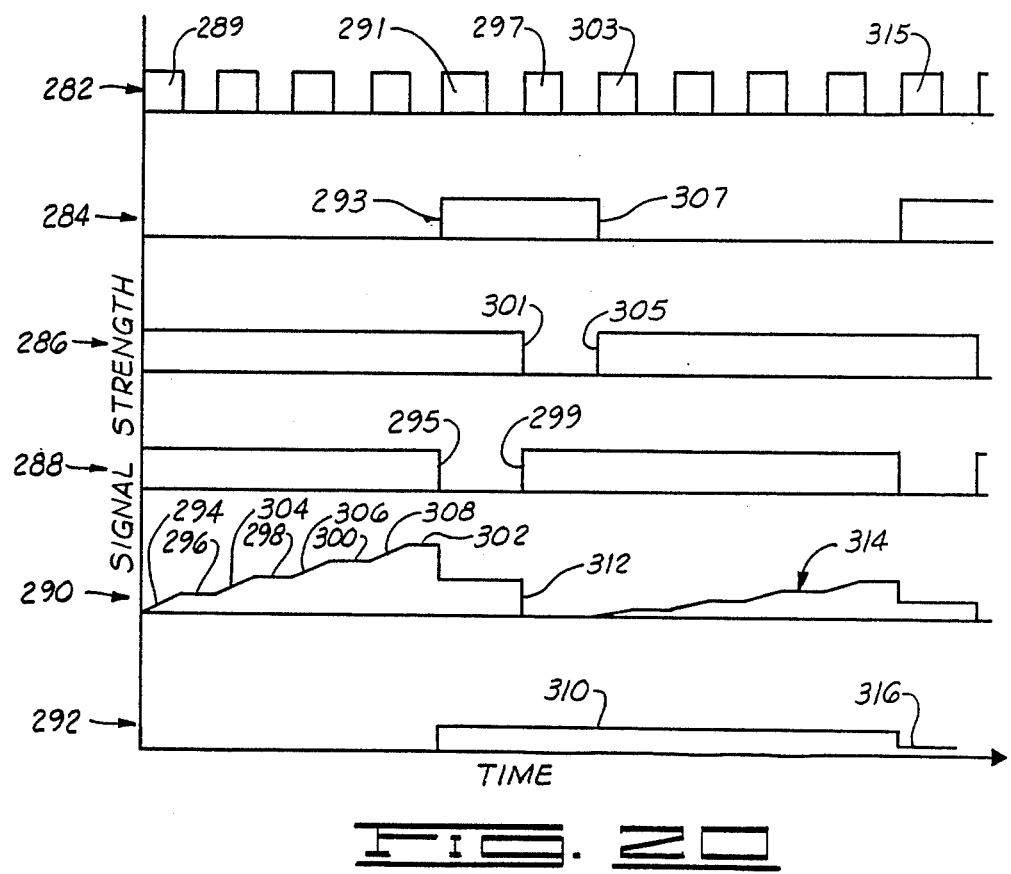
FIG. 20 is a timing diagram illustrating the operation of the timing circuit of the electromagnet control circuit.

The construction of the timing circuit 146 has been particularly illustrated in FIG. 15 and FIG. 20 has been included to illustrate the operation of the timing circuit 146, the latter of these two Figures showing the form of electrical signals that appear at various times and at selected points in the electromagnet control circuit 72. Referring first to FIG. 15, the timing circuit is comprised of a type CD4017 Johnson counter 240; that is, a counter that is constructed to pass a positive voltage serially along a plurality of output terminals in response to a series of pulses received by the counter. Such pulses are provided on the conductor 148 from the astable multivibrator 120, the conductor 148 being connected to the clock input terminal 242 of the counter 240 The counter 240 can be reset by a positive voltage supplied to a reset terminal 244 and the reset terminal 244 is connected to an output terminal 246 of the counter 240 that is the seventh of the output terminals to become positive in response to a series of pulses supplied to the clock terminal 242 of the counter 240 following reset of the counter 240. Thus, in response to a continuous stream of pulses received at the clock terminal 242 of the counter 240, a repeating operation of the counter 240 will occur in which a positive voltage is sequentially passed along six output terminals of the counter 240. The first four of these output terminals, indicated at 248–254 in FIG. 15 are connected to the input terminals 256–262 of a type 4002 NOR gate 264 and the output terminal 266 of the NOR gate 264 is connected to the conductor 222 leading to the switch 220 in the integrator 208. (The type 4002 NOR gate is an integrated circuit upon which two NOR gates are constructed. Only one of these NOR gates in the integrated circuit is used in the operation of the timing circuit so that it is useful to refer to such integrated circuit as the NOR gate).

The fifth and sixth output terminals of the counter 240 to become positive in response to a series of pulses received by the counter 240 at the clock terminal 242 following reset, the fifth output terminal being indicated at 268 in FIG. 15 and the sixth output terminal being indicated at 270 in FIG. 15, are connected to two inverters of a type CD4069 hex inverter integrated circuit 272 at input terminals 274 and 276 of the circuit 272 and output terminals 278 and 280 of the circuit 272, corresponding to the input terminals 274 and 276, respectively are connected to the conductors 224 and 238 that extend, respectively, to the switches 218 in the integrator 208 and 234 in the sample and hold circuit 228.

Referring now to FIG. 20, shown therein is a graph illustrating electrical signals at selected points in the electromagnet control circuit 72 following reset of the counter 240. For each of the curves shown in the graph, signal strength (voltage) is plotted along the ordinate and time, common to all the curves, is plotted along the abscissa. The uppermost curve 282 is the voltage at the output of the astable multivibrator 120 so that the uppermost curve 282 illustrates a series of pulses that are simultaneously supplied to the clock terminal 242 of the counter 240 and to the infrared transmitter 142. For each of these pulses, a positive voltage will be shifted along the line of output terminals of the counter 240 and, since the graph has been drawn to illustrate signals immediately following reset of the counter 240, the first output terminal 248 of the counter 240 becomes positive with the rise of the first pulse 289 of the curve 282. Thus, a positive voltage will be supplied to the input terminal 245 of the NOR gate 264 during the duration of the first pulse 289 of the curve 282 and up to the rise of the second pulse of the curve 282. In response, the output terminal 266 of the NOR gate 264 will be substantially grounded as illustrated in the second curve at 284 in FIG. 20. On the other hand, the fifth and sixth output terminals, 268 and 270 respectively, of the counter 240 will be substantially grounded during the first pulse so that the inputs 274 and 276 of the circuit 272 will be substantially grounded Thus, positive voltages appear at the inverter outputs 278 and 280 during the first pulse 289 as illustrated by the curves 286 and 288 respectively in FIG. 20.

Since the inverter output terminals 278 and 280 of the circuit 272 are connected to the switches 218 and 234 in the integrator and sample and hold circuit respectively and since the switches 218 and 234 open in response to positive voltages supplied thereto, the switches 218 and 234 will be open during the first pulse supplied to the counter 240 by the astable multivibrator 120. Similarly, since the output terminal 266 of the NOR gate 264 is substantially at ground voltage and is connected to the switch 220 of the integrator 208, the switch 220 of the integrator 208 will be closed during the first pulse provided by the astable multivibrator. Such conditions of the switches 218, 220 and 234 will continue until the rise of the fifth pulse 291 provided by the astable multivibrator 120 because of the connection of the first four output terminals of the counter 240 to the NOR gate 264 which controls the switch 220 and because of the control of the switches 218 and 234 via the fifth and sixth output terminals of the counter 240. With the rise of the fifth pulse 291 produced by the astable multivibrator 120, the voltage at the fourth output terminal 254 of the counter 240 drops to zero so that all four input terminals 256–262 of the NOR gate 264 become substantially grounded to produce a positive voltage at the output terminal 266 of NOR gate 264. This voltage rise is transmitted to the switch 220 of the integrator 208, as indicated at 293 in FIG. 20, to open the switch 220. Concurrently with the drop in voltage at the fourth output terminal of the counter 240 with the rise of the fifth pulse produced by the astable multivibrator 120, a positive voltage appears at the fifth output terminal 268 of the counter 240 and is transmitted to the input terminal 274 of the invertor 272 to cause the output terminal 280 of the invertor 272 to become substantially grounded, as shown at 295 for the curve 288, so that the switch 234 in the sample and hold circuit 228, such switch being connected to the inverter output terminal 280 of the circuit 272, is closed. Thus, with the rise of the fifth pulse 291 provided by the astable multivibrator 120, the integrator 208 is isolated from the difference amplifier 196 and a portion of any charge that might have accumulated in the integrator 208 is transferred to the sample and hold circuit 228.

With the rise of the sixth pulse 297 produced by the astable multivibrator 120, the voltage at the fifth output terminal 268 of the counter 240 drops so that the inverter input terminal 276 of the circuit 272 is substantially grounded and a positive voltage appears at the inverter output terminal 280 of the circuit 272, as shown at 299 for the curve 288, and is transmitted to the switch 238 of the sample and hold circuit 228 to open the electrical connection between the integrator 208 and the sample and hold circuit 228 Concurrently, a positive voltage appears at the sixth output terminal of the counter 240 and is transmitted to the inverter input terminal 274 of the circuit 272 to cause the inverter output terminal 278 of the circuit 272 to become substantially grounded as shown at 301 in the curve 286 in FIG. 20. Since the switch 218 of the integrator 208 is connected to the inverter output terminal 278 of the circuit 272, the switch 218 closes to discharge the capacitor 216 of the integrator 208 during the sixth pulse provided by the astable multivibrator 120.

With the rise of the seventh pulse 303 provided by the astable multivibrator, the counter 240 is reset so that the sixth output terminal 270 of the counter 240 become grounded, causing a rise 305 in the voltage supplied to the switch 218, thereby opening the switch 218 of the integrator 208 and a positive voltage appears at the first output terminal 248 of the counter 240 to again disable the NOR gate 264, as illustrated at 307, and close the switch 220 of the integrator 208. The seventh pulse 303 is thus equivalent to the first pulse 289 so that the pattern of voltages appearing at the switches 220, 218 and 234 of the integrator 208 and sample and hold circuit 228 repeats for every six pulses delivered by the astable multivibrator 120 and such pattern is as follows For the first four pulses of each series of six pulses delivered by the astable multivibrator, the switch 220 of the integrator 208 is closed and the switch 218 of the integrator 208 is open so that the integrator can accumulate a charge porportional to the integral of a signal at the output of the difference amplifier 196 beginning with the rise of the first pulse of each series of six pulses generated by the astable multivibrator 120. With the rise of the fifth pulse of each series of six pulses, the switch 220 of the integrator 208 opens and the switch 234 of the sample and hold circuit 228 closes so that the charge accumulated in the integrator 208 is partially transferred to the sample and hold circuit 228. With the rise of the sixth pulse, the switch 234 of the sample and hold circuit 228 opens and the switch 218 of the integrator 208 closes so that the sample and hold circuit 228 is isolated from the integrator 208 and the capacitor 216 of the integrator 208 is discharged for the accumulation of a new charge in the integrator during the next succeeding four pulses generated by the astable multivibrator. Such accumulation begins with the first of the next series of six pulses delivered by the multivibrator 120, the rise of such first pulse of the next series causing the switch 218 in the integrator 208 to open and the switch 220 to close to reconnect the integrator 208 to the difference amplifier 196.

Also shown in FIG. 20 are curves illustrating the charge accumulated in the integrator 208 and the charge stored in the sample and hold circuit 228 during a time period corresponding to eleven pulses produced by the astable multivibrator 120 beginning with the reset of the counter 240 that occurs with the rise of the first of the series of pulses shown in the curve 282. The curve 290 of FIG. 20 is a graphical depiction of the charge accumulated in the integrator 208 and curve 292 is a graphical depiction of the charge stored in the sample and hold circuit 228. It has been assumed in drawing curve 292 that the impellor has been at the null position thereof for a period of time prior to the first pulse 289 so that no charge is stored in the sample and hold circuit 228 when the first pulse 289 occurs.

Concurrently with the generation of each pulse by the astable multivibrator 120, a pulse of infrared radiation is emitted by each of the light emitting diodes 158 and 160 and such radiation pulses are directed across the inlet passages 52 and 54 to impinge upon the phototransistors 174 and 176 of the infrared receivers 178 and 180. If, prior to the first of the pulses shown in FIG. 20, the impellor 42 has been located at the null position thereof, the phototransistors 174 and 176 will have been equally illuminated so that equal electrical signals will have been continuously impressed on the inverting and non-inverting inputs of the operational amplifier 198 of the difference amplifier 196 with the result that no signal will have appeared on the conductor 212 from the output of the difference amplifier 198 for any of the pulses that have been generated by the astable multivibrator 120 immediately prior to the pulses illustrated in FIG. 20. Accordingly, as the first pulse of the curve 282 rises, no charge will have been previously accumulated by the integrator 208 and no charge will have been stored in the sample and hold circuit 228. Assuming that the impellor 42 becomes displaced from the null position immediately prior to the rise of the first pulse of the curve 282, emission of a pulse of infrared radiation during the first such pulse of the curve 282 will result in unequal illumination of the phototransistors 174 and 176. As a result, during the first pulse 289, the difference amplifier 196 will receive unequal signals from the two infrared receivers 178, 180 so that the difference amplifier 196 will provide a non-zero signal on the conductor 212 that provides an input to the integrator 208. The integral of this signal is accumulated in the integrator 208 as indicated by the portion 294 of the curve 290 in FIG. 20. During the interim between the first and second pulses of curve 282 in FIG. 20, no power is supplied to the light emitting diodes 158 and 160 so that the phototransistors of the infrared receivers 178 and 180 are not illuminated. Thus, during the interim between these first two pulses, and between any other pair of pulses, both inputs of the difference amplifier 192 are effectively grounded so that no accumulation of charge occurs in the integrator 208 between pulses produced by the astable multivibrator 120 as indicated by the flat portions 296-302 of the curve 290 in FIG. 20. During the second, third and fourth of the first six pulses of the series shown in the curve 282, the light emitting diodes 158, 160 will again provide pulses of infrared radiation directed across the pump input passages 52 and 54 and, assuming the impellor 42 remains displaced from the null position in the same direction as the displacement of the impellor 42 from the null position during the first pulse 289, the phototransistors of the infrared receivers 178 and 180 will remain unequally illuminated so that the difference amplifier 196 will again receive unequal signals from the infrared receivers to provide a signal, having the same polarity as the signal provided during the first pulse 289 to the integrator 208. As the result, additional accumulations of charge in the integrator 208 will occur for the second, third and fourth pulses shown in the curve 282 of FIG. 20 as indicated by the sloped portions 304-308 of the curve 290. With the rise of the fifth pulse of the series shown in the curve 282, a portion of the charge accumulated in the integrator 208 will be transferred to the sample and hold circuit via the above described opening of the switch 220 and closure of the switch 234 so that a charge will appear on the capacitor 232 of the sample and hold circuit 228 as indicated by the portion 310 of the curve 292. Such charge will remain on the capacitor 232 until the switch 234 of the sample and hold circuit 228 is again closed. That is, such charge will remain on the capacitor 234 for a series of six pulses delivered by the astable multivibrator beginning with the rise of the fourth pulse of each series of six pulses utilized in the control of the switches of the integrator 208 and sample and hold circuit 228. With the rise of the last pulse of the first six member series shown in the curve 282, the switch 218 is closed to reset the integrator as indicated by the drop 312 of the curve 290. With the rise of the seventh pulse 303, such pulse being the first of a new series of six pulses, a new charge is accumulated in the same stepwise fashion in the integrator 208 for the next four pulses produced by the astable multivibrator 120 as has been indicated by the zig zag portion 314 of the curve 290 in FIG. 20. (The portion 314 of the curve 290 has been drawn with an amplitude that is reduced with respect to the portion of the curve 290 produced by the first four pulses shown at 282 to reflect the effect of the onset of impellor repositioning that occurs when a charge is transferred into the sample and hold circuit with the pulse 291.) With the rise of the fifth pulse of the second series of six pulses, indicated at 315 for curve 282 in FIG. 20, the charge that is accumulated during the first four pulses of the second series of six pulses is transferred to the sample and hold circuit 228 as indicated by the portion 316 of the curve 292 and such charge remains stored in the sample and hold circuit for six of the pulses produced by the astable multivibrator 120 beginning with the rise of the fifth pulse of each series of six pulses generated by the multivibrator 120. Thus, for the first four of each series of six pulses produced by the astable multivibrator, a charge is accumulated in the integrator 208 and is transferred to the sample and hold circuit beginning with the fifth pulse of the series. With the rise of the sixth pulse, the integrator is reset and a new accumulation begins with the rise of the first pulse of the next series of six pulses. The sample and hold circuit receives a portion of each accumulation with the rise of the fifth pulse of the series and stores such portion for six pulses so that the charge stored in the sample and hold circuit 228 reflects the average displacement of the impellor 42 during a time period corresponding to six pulses produced by the astable multivibrator just prior to the transferal of charge from the integrator 208 to the sample and hold circuit 228. Thus, the magnetic control circuit 72 develops a signal which is indicative of the location of the impellor 42 during a time period corresponding to six pulses of the astable multivibrator and such signal is used to correct the location of the impellor during an equal time interval in which a new correction signal is generated. Such correction is effected by first and second controllers, 318 and 320 respectively and a power amplifier 322 as will now be discussed.

The sample and hold circuit 228 provides a signal at the output of the operational amplifier 230 the circuit 228 includes that is proportional to the charge on the capacitor 232 and such signal is transmitted to the first controller 318 via a conductor 324. The first controller 318, which has been particularly illustrated in FIG. 16, is an amplifier that includes an operational amplifier 326 and a feedback network made up of a 2.2 nanofarad capacitor 328 and a 100 kilohm resistor 330 connected in parallel between the output terminal of the operational amplifier 326 and the inverting input terminal thereof.

The signal from the sample and hold circuit 228 is transmitted via a 69.8 kilohm resistor 332 and 47 nanofarad capacitor 334 to the inverting input terminal of the operational amplifer 326 and a summing network, comprised of two 210 kilohm resistors 336, 338 and one 150 kilohm resistor 340, is connected to the non-inverting input of the operational amplifier 326 at a junction between the three resistors 336-340. The opposite end of the resistor 340 is grounded so that the signal supplied to the non-inverting input terminal of the operational amplifier 326 is the sum of two signals introduced via the two resistors 336 and 338. The signal supplied via the resistor 336 is derived from a zero-adjust potentiometer 342, the resistor 336 being connected to the wiper arm of the potentiometer 342. The potentiomenter 342 can suitably be a 10 kilohm resistor and the ends of the potentiometer 342 can suitably be connected to the power supply so that a 15 volt signal is supplied to one end of the potentiometer 342 and a signal of −15 volts is supplied to the other end thereof. The second signal supplied to the non-inverting input of the operational amplifier 326 is derived from the second controller 320 via a conducting path 344 shown in FIGS. 8, 16 and 17.

Figures 16, 17:
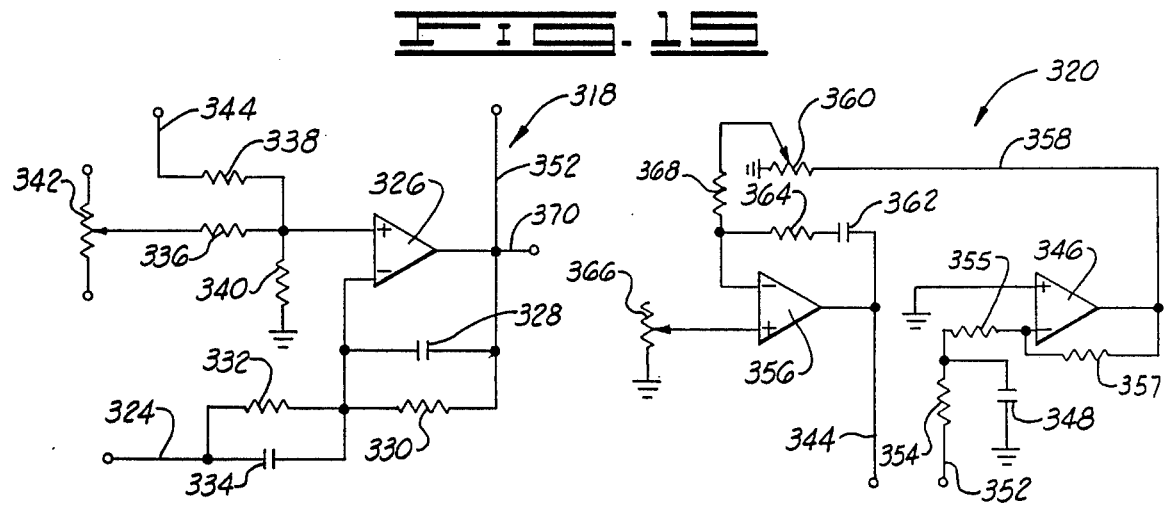
FIG. 16 is a circuit diagram for controller number 1 of the electromagnet control circuit.
FIG. 17 is a circuit diagram for controller number 2 of the electromagnet control circuit.

The operational amplifier 326 is suitably one of four operational amplifiers of a type TL084 integrated circuit and two of remaining operational amplifiers of such integrated circuit are used in the second controller 320 as shown in FIG. 17. In particular, the second controller 320 is comprised of a low pass filter that, in turn, is comprised of one of the remaining operational amplifiers of the TL084 integrated circuit, indicated at 346 in FIG. 17, a capacitor 348 and resistors 354 and 355, 357. The non-inverting input of the operational amplifier 346 is connected to the circuit ground and the inverting input of the operational amplifier 346 is connected via resistors 354 and 355, connected in series, to the output of the first controller 318 via conductor identified by the numeral 352 in FIGS. 16 and 17. The capacitor 348 is connected between the circuit ground and the juncture of the resistors 354 and 355 to filter high frequency components of the signal present in the output of the first controller 318 and the resistor 357 is connected between the inverting and output terminals of the operational amplifier 346 as a feedback resistor as is conventional.

The output signal from the filter that includes the operational amplifier 346 is provided to one end of a 0–250 kilohm potentiometer 360, the other end of which is grounded, and a portion of this signal is provided to the inverting input of an operational amplifier 356 via a resistor 368. Feedback for the operational amplifier 356 is provided by a 100 nanofarad capacitor 362 and a 10 kilohm resistor 364 that are connected between the output terminal of the operational amplifier 356 and the non-inverting input terminal thereof. The non-inverting input of the operational amplifier 356 is connected to the wiper arm of a 500 kilohm input current compensation potentiometer 366, one end of the potentiometer 366 being grounded. Conductor 344, to which the resistor 338 shown in FIG. 16 is connected, is also connected to the output terminal of the operational amplifier 356 of the second controller 320 so that one of the two signals that are supplied to the non-inverting input terminal of the operational amplifier 326 of the first controller 318 is provided by the second controller 320 operating in response to the output signal of the first controller 318.

The function of the second controller 320 is to minimize the consumption of energy by the impellor suspension system by effecting the above mentioned limitation on the use of the electromagnet 70 to stabilization of the support of the impellor 42 by the permanent magnet impellor support assembly 68. As has been noted, the permanent magnets of the assembly 68 can be used to support the impellor 42 against a static axial force by shifting the position at which the impellor 42 is supported in the housing 44 from the null position, defined as an equilibrium position for the impellor under only those forces exerted thereon by the permanent magnet impellor support assembly 68, to a control position which is an equilibrium position for the impellor under the permanent magnet forces and an additional axial force that might be exerted on the impellor 42. Should such an additional axial force be exerted on the impellor 42 while the position of the impellor 42 is stabilized at the null position, the signals provided to the difference amplifier 196 by the infrared receivers 178, 180 would include a direct current component, such component arising from a persistent small shift in the position of the impellor 42 in the direction of the static axial force as opposed to random variations in position of the impellor 42 about the null position Such direct current component would be integrated and stored in the sample and hold circuit 228 so that an output signal from the first controller 318 would also contain a direct current component. Such component is transmitted to the operational amplifier 356 of the second controller 320 by transmitting the output signal from the first controller 318 to the filter circuit of the second controller 320 constructed on the operational amplifier 346 and connecting the output of such filter circuit to the operational amplifier 356. The operational amplifier 356 then injects a signal into the non-inverting input terminal of the operational amplifier 326 of the first controller 318 to temporarily increase the current at the output terminal of the operational amplifier 326 of the first controller 318. Elimination of the direct current component occurs by providing a current to the electromagnet 70 that will shift the impellor 42 to the control position in which the permanent magnet impellor support assembly 68 will exert a force on the impellor 42 that balances permanent magnetic and all other long term axial forces thereon.

The establishment of the control position for the impellor 42 that is displaced from the null position thereof, or from a previously established control position, entails an initial increase in the current that is supplied to the electromagnet 70 to move the impellor 42 against a static axial force exerted thereon so that the energy saving provided by the second controller 320 occurs only when the static axial force persists for a length of time sufficient for the initial additional expenditure of energy to be exceeded by the additional energy that would have to be supplied to the electromagnet 70 to maintain the impellor 42 at the null position or a previously established control position in the presence of the static axial force. To insure that the second controller 320 will react only to long term axial forces that persist long enough to outweigh the energy required to establish a new control position for the impellor 42, the time constant for the capacitor 348 and resistor 354 of the second controller 320 is selected, in the adaptation of the invention to the blood pump application, to be approximately one to two seconds. Such time constant can conveniently be achieved by selecting the capacitor 348 and the resistor 354 to have values of one or two microfarads and one megohm respectively.

Figure 18:
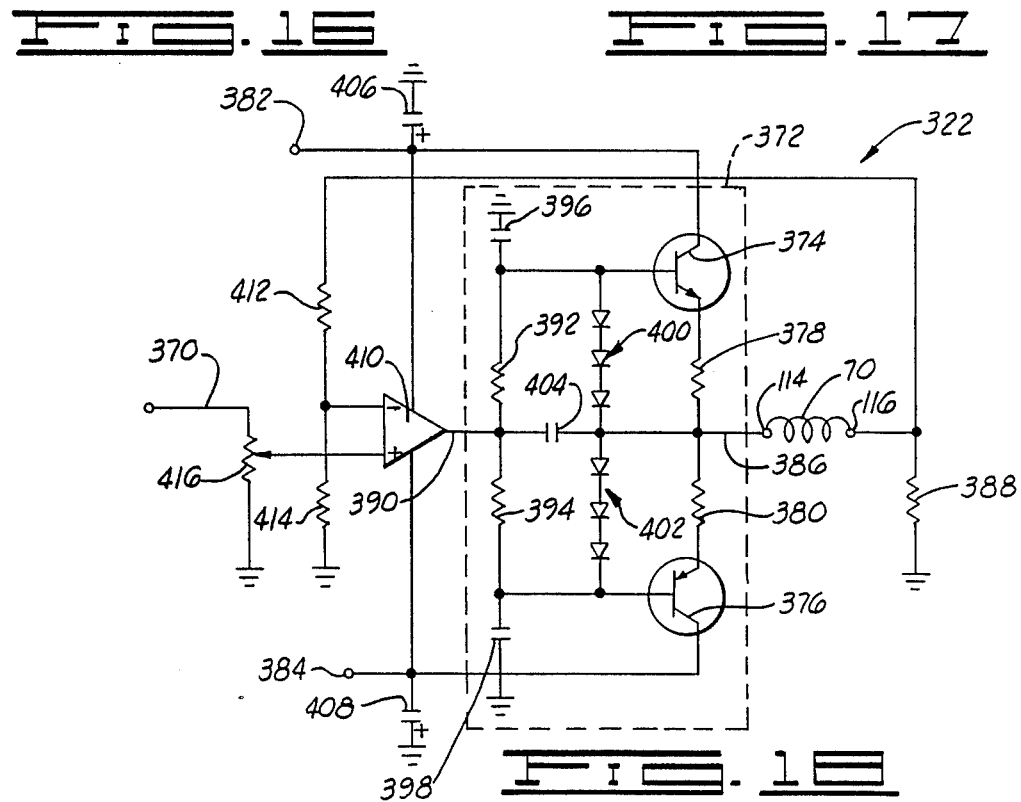
FIG. 18 is a circuit diagram of the power amplifier of the electromagnet control circuit.
Figure 13:
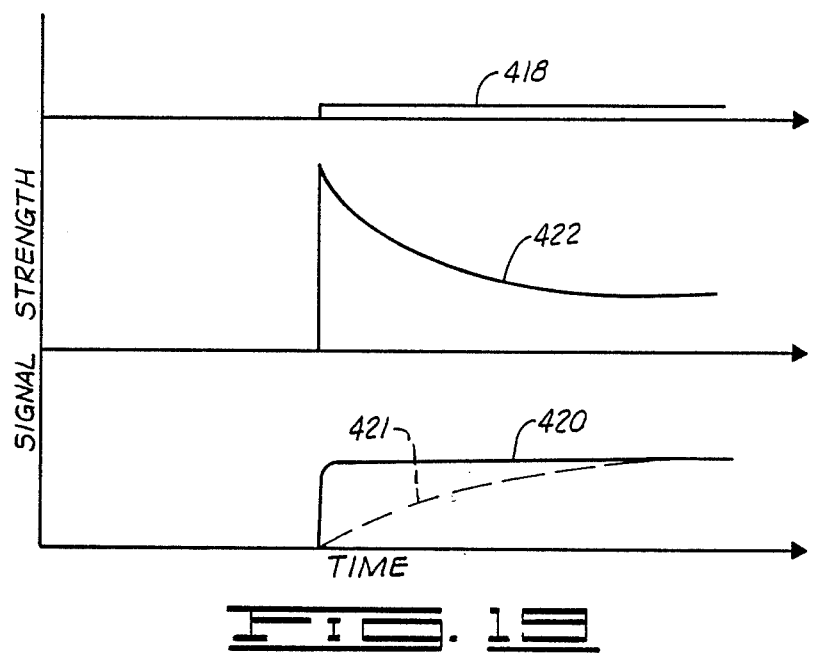

The power amplifier 322, which has been particularly illustrated in FIG. 18, receives the output of the first controller 318 via a conductor 370 that is connected to the output terminal of the operational amplifier 326 and provides a control current to the electromagnet 70. The power amplifier 322 is constructed to drive the electromagnet 70 in accordance with the current, rather than the voltage, needed to reposition the impellor 42 should the impellor 42 become displaced from the control position so that the electromagnet control circuit 72 responds rapidly to shifts in position of the impellor despite the inductive load; that is, the electromagnet 70, driven by the electromagnet control circuit 72. To this end, the power amplifier 322 is comprised of two stages: a power stage indicated in dashed lines at 372 in FIG. 18 and a control stage (not numerically designated in the drawings) that drives the power stage in a manner that will result in current, rather than voltage, control of the power amplifier 322.

Referring first to the power stage 372, such stage is a conventional push-pull amplifier comprised of an npn power transistor 374 (preferably a type MJ3001) and a pnp power transistor 376 (preferably a type MJ2501) having emitters connected together via two 0.27 ohm resistors 378 and 380. The collectors of the transistors 374 and 376 are connected to positive and negative supply terminals, 382 and 384 respectively, and the output of the power stage 372 at the junction of the two resistors 378 and 380 is connected via a conductor 386 to the input terminal 114 of electromagnet 70. The input terminal 116 of the electromagnet 70 is connected via a 0.47 ohm resistor 388 to the circuit ground. The input to the power stage is at a conductor 390 that is connected to the bases of the transistors 374 and 376 via 2.2 kilohm resistors 392 and 394. The bases of the transistors 374 and 376 are also connected to the circuit ground via 33 nanofarad capacitors 396 and 398 and to the output provided by the conductor 386 via a plurality of diodes 400 for the transistor 374 and a plurality of diodes 402 for the transistor 376. A 10 nanofarad capacitor 404 is connected between the conductors 386 and 390 that provide the output and input respectively for the power stage 374 and 100 microfarad capacitors 406 and 408 are connected between the collectors of the transistors 374 and 376 respectively and the circuit ground to prevent a signal from the power stage output from being introduced into the control stage of the power amplifier 322.

The control stage of the power amplifier 322 is comprised of an operational amplifier 410 having an output terminal that is connected to the conductor 390 forming an input to the power stage 372 and an inverting input terminal that is connected to a voltage divider, comprised of serially connected 100 kilohm and 10 kilohm resistors 412 and 414 that are connected in parallel across the 0.47 ohm resistor 388 so that a portion of the voltage across the resistor 388 is injected into the inverting input terminal of the operational amplifier 410. The non-inverting input terminal of the operational amplifier 410 is connected to the wiper arm of a 100 kilohm potentiometer 416, one end of which is connected to the circuit ground and the other end of which is connected to the conductor 370 leading to the output terminal of the operational amplifier 326 of the first controller 318.

The above-described construction of the power amplifier 322 results in the power amplifier 322 having characteristics which have been illustrated in FIG. 19 in which signal strengths at several places in the circuit 72 have been plotted versus time. In the upper of the three graphs of such Figure, a typical output for the first controller 318 has been plotted as the curve 418 which illustrates the voltage at the output terminal of the operational amplifier 326 (the ordinate of the upper graph) as a function of time, time being plotted along the abscissa, for an assumed step output. For effective control of the position of the impellor 42, it is desired that the force the electromagnet 70 exerts on the permanent magnets 78 and 80 mounted on the impellor 42 follow the curve 418 so that, since the magnetic field produced by the electromagnet 70 is proportional to the current therethrough, it is desirable that the current through the electromagnet 70 closely approximate the curve 418 shown in FIG. 19. Such current is shown by the curve 420 in FIG. 19 in the lowermost graph of such Figure, the current through the electromagnet 70 being plotted as the ordinate in the lowermost graph in FIG. 19 as a function of time along the abscissa. (For purposes of comparison, the current that would result for a constant voltage applied to the electromagnet 70 has been shown in dashed lines at 421 in FIG. 19.) To achieve this correspondence between the current through the electromagnet 70 and the voltage at the output terminal of the operational amplifier 326 of the first controller 318, the voltage at the output terminal of the operational amplifier 410 of the control stage of the power amplifier 322 is made proportional to the difference between the voltage across the resistor 388 of the power amplifier 322 and the voltage supplied to the power amplifier 322 by the first controller 318. Thus, should the first controller 318 deliver a signal such as has been illustrated by the curve 418 in FIG. 19 to the power amplifier 322; that is, a signal having a step preceeded by a null signal, the input to the operational amplifier 410 of the power amplifier 322 will, initially, be large corresponding to the absence of a voltage across a resistor 388 by means of which the electromagnet 70 is grounded. Thus, the voltage at the output of the operational amplifier 410 of the power amplifier 322 will initially be a large value, as indicated by the curve 422 in FIG. 19, to overcome inductive effects that tend to delay the establishment of a current through the electromagnet 70. Such voltage then decreases in response to the establishment of the current through the electromagnet 70 so that, should the initial signal indicated by the curve 418 persist, the voltage at the output terminal of the operational amplifier 410 will eventually attain a steady state value as indicated by the center graph of FIG. 19. By causing the voltage at the input of the power stage 372 of power amplifier 322 to be large at such times that the current through the electromagnet 70 is small, the current through the electromagnet 70 is caused to substantially follow the signal that the first controller 318 provides to the power amplifier 322 resulting in a rapid response time for the power amplifier 322 that prevents the impellor from making wide excursions from the control position that will require large amounts of energy to correct. Thus, the current, as opposed to voltage, control that is built into the power amplifier 322 additionally contributes to a low power consumption for the suspension system of the present invention.

In addition to the above-described magnetic suspension assembly, the apparatus 40 comprises a rotor (impellor in the case of a pump) drive assembly (not numerically designated in the drawings) that spins the rotor (impellor in the case of a pump) 42 about the rotor (impellor in the case of a pump) axis 60. One preferred form of the rotor drive assembly, particularly useful in the case in which the apparatus 40 is a pump having the form shown in FIG. 1, has been illustrated in FIGS. 21-26.

Figure 21:
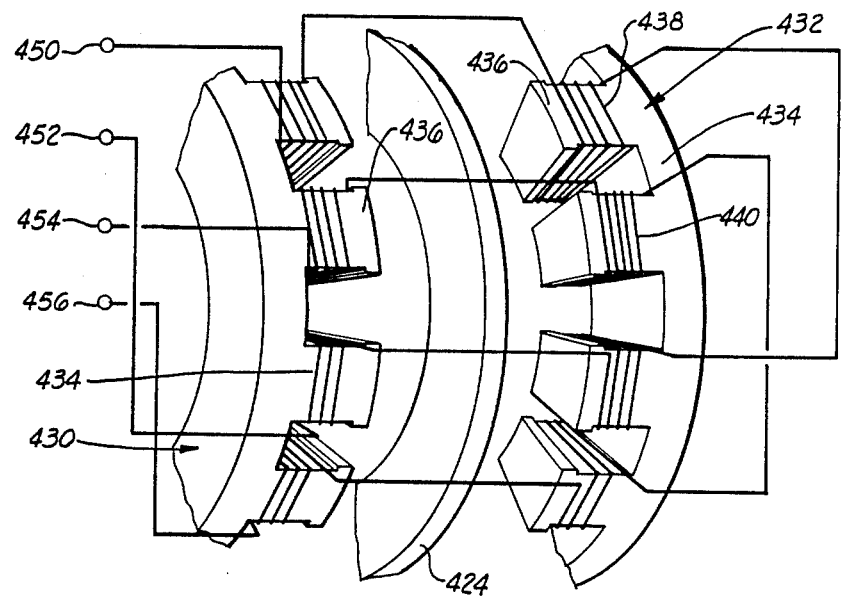
FIG. 21 is an isometric view of one preferred arrangement of stator coils used to rotate the impellor of the pump shown in FIG. 1.

Referring first to FIG. 21, and with additional reference to FIG. 2, the impellor drive assembly is comprised of a shorting ring 424 that is disposed within the impellor 42 to extend in a circle about the impellor axis 60 as shown in FIG. 2. As can also be seen in FIG. 2, the shorting ring 424 is positioned axially midway between the ends 164, 168 of the impellor 42 so that the portions of both the magnetic suspension assembly and the impellor drive assembly that are mounted on the impellor 42 are symmetrically positioned thereon. That is, these portions of the two assemblies exhibit cylindrical symmetry about the impellor axis 60 and bilateral symmetry about a plane perpendicular to the axis 60 midway between the ends of the impellor 42. This symmetry of portions of the magnetic suspension and rotor drive assemblies mounted on the impellor 42 is utilized to provide a further minimization in the power requirements of the apparatus 40 as will now be described.

As shown in FIG. 2, a cavity 426 is formed in central portions of the impellor 42 and such cavity has the same symmetry characteristics as the shorting ring 424 and the magnets 78 and 80 mounted on the impellor 42. Thus, since the two end portions 62 and 64 of the impellor 42 are identical, to again have the same symmetry characteristics, the combined center of gravity of the impellor 42 and portions of the drive and suspension assemblies thereon is located at the geometric center of the impellor 42; that is, at the point indicated at 428 in FIG. 2. Similarly, because of the symmetry of the impellor 42, the center of buoyancy of the impellor 42 is also located at the point 428 with the net result that the gravitational force and buoyant force on the impellor 42 cannot produce a couple on the impellor 42. Rather, at most, these two forces can produce only a resultant force that extends along the vertical The size of the cavity 426 in the impellor 42 is selected to adjust the average specific gravity of the impellor 42 and portions of the magnetic suspension and rotor drive assemblies on the impellor 42; that is, a specific gravity determined by dividing the weight of the impellor and portions of the magnetic suspension and drive assemblies mounted thereon by the volume of the impellor 42, to match the specific gravity of a liquid which is pumped by the pump 40. In the case in which the pump 40 is used as a blood pump, such average specific gravity is approximately 1.056 to match the specific gravity of blood The matching of the average specific gravity of the impellor and portions of the magnetic suspension and impellor drive systems mounted thereon, achieved in part by using two permanent magnets 78 and 80 in the impellor 42 as part of the magnet suspension assembly, and the positioning of the center of gravity of the impellor 42 and portions of these two assemblies mounted thereon at the center of buoyancy of the impellor 42 has the result that the impellor 42 reacts to accelerations of the pump 40 in precisely the same manner that an equal volume of blood having the same position as the impellor 42 would react to an acceleration of the pump 40. Thus, should the pump 40 be implanted in a person, no additional energy expenditure by the magnetic suspension assembly would be required to accelerate the rotor 42 should the person move to give rise to an acceleration of the pump housing 44. Rather, the work that would have to be done on the impellor 42 to cause the impellor 42 to move with the housing 44 would be supplied by the internal walls of the housing 44 in the same manner that such work is supplied by the internal walls of the housing 44 to cause blood within the housing 44 to be accelerated with the housing 44. Thus, again, the energy required to be expended by the magnetic suspension assembly is only that energy required to stabilize the support of the impellor 42 by the permanent magnet impellor support assembly 68. Since, as has been noted, such stabilization is accomplished by maintaining the impellor 42 substantially at an equilibrium position, very little energy is required to stably support the impellor 42 within the impellor chamber 50.

As shown in FIGS. 2 and 21, the impellor (rotor) drive assembly for the pump 40 further comprises a stator (not numerically designated in the drawings) that includes two ferromagnetic pole pieces 430 and 432 positioned to opposite sides of the shorting ring 424. Each of the pole pieces 430, 432 comprises a ring portion 434 disposed coaxially with the shorting ring 424 and a plurality of projections 436 that extend from the ring portion 434 toward the shorting ring 424. In one preferred embodiment of the invention, each pole piece is provided with twelve projections 436, equally spaced about the ring portion 434, and the pole pieces 430, 432 are positioned to axially align the projections 436 of the pole piece 432 with the projections of the pole piece 430. Two coils, 438 and 440, are wrapped on the projections 436 as shown in FIG. 21; that is, the coil 438 is serially wrapped about every other set of facing projections with the senses of the windings of the coil 438 from one set of projections 436 to the next being selected such that the magnetic field reverses in direction from one set of projections wrapped with the coil 438 to the next set of such projections 436. The coil 440 is similarly wrapped on the remaining projections 436 of the pole pieces 430, 432 so that the shorting ring 424 can be magnetically rotated, to rotate the impellor 42, by supplying alternating currents having the same frequency and amplitude, but phase shifted by 90°, to the coils 438 and 440.

In addition to the stator formed by the pole pieces 430 and 432 and the coils 438 and 440, the impellor drive assembly for the apparatus 40 comprises a rotor control circuit 458 which has been illustrated in block form in FIG. 22. In such Figure and in FIG. 21, the coils 438 and 440 have been indicated as having terminals 450 and 452 (for the coil 438) and 454 and 456 (for the coil 440) to indicate the manner in which the coils 438 and 440 are connected to the rotor control circuit 458. As can be seen in these Figures, the terminals 452 and 456 of the coils 438 and 440 respectively are connected to the circuit ground so that rotation of the impellor 42 can be effected by providing phase shifted, alternating current signals to the terminals 450 and 454.

It is contemplated in the present invention that the rotation rate of the rotor 42; that is, the impellor 42 in the pump adaptation of the invention, is to be controlled in accordance with a preselected relationship between such rotation rate and the value of a measurable physical quantity. In particular, where the invention is adapted for use as a blood pump, the rotation rate of the impellor 42 can be controlled to cause the pump to mimic the physiological pumping characteristics of the natural heart. Such characteristics are embodied in the so-called Frank-Starling effect which relates the pumping rate of each half of the natural heart and the change in pressure across each half of the heart to pressure at the inlet of each half of the heart. The effect thus lumps the interaction between each half of the heart and the remainder of the body into a single parameter, inlet pressure, that can be measured so that the interaction between the heart and the body can be duplicated in an artificial heart or a heart assist device by controlling the flow of blood through a pump that replaces or assists the heart to mimic this effect.

To this end, and as shown in FIG. 2, a socket 464 is formed in the wall of the first inlet passage 52 to receive a pressure sensor 466, a suitable sensor being one of the model 1800 series pressure transducers manufactured by Foxboro/ICT of San Jose, California, such transducer being selected to cover a range of pressure consistent with the particular application to which a pump that includes the rotor suspension and rotation system of the present invention is adapted. These transducers are analog devices and the rotor control circuit further comprises a conventional A/D convertor 468 to which the sensor 466 is connected, via conductor 467, so that each pressure sensed by the sensor 466 is expressed as an eight bit binary number at eight output terminals of the convertor 468. Both the frequency and amplitude of the alternating current signals supplied to the coils 438 and 440 are controlled in the present invention in accordance with the eight bit binary number that appears at the output terminals of the A/D convertor 468.

To establish appropriate values for the frequency and amplitude of the signals transmitted to the coils 438 and 440, the eight bit number at the output terminals of the A/D convertor 468 is transmitted, via a bus indicated by a broad arrow 470 in FIGS. 22 and 23, to the input terminals of an encoder 472 that has been shown in more detail in FIG. 23. (The rotor control circuit 458 is a hybrid analog-digital circuit. In order to clearly bring out the operation of this circuit, the convention has been adopted in the drawings of illustrating buses which transmit digitally expressed signals as broad arrows and conductors which transmit analog signals as lines.) As shown in FIG. 23, the encoder 472 is comprised of a first memory device 474 which is preferably a type MM2716 PROM, the bus 470 being connected to the address terminals of the device 474. (For clarity of disclosure, integrated circuits used in the control circuit 458 that have been selected to provide specific functions have been identified by manufacturer's type number in FIGS. 23-25. The identified integrated circuits, and their interconnections, provide a preferred embodiment of the control circuit 458 but it will be recognized that substitutions can be made for the integrated circuits so identified.) The device 474 is programmed, in a manner to be discussed below, so that the digital number appearing at the data terminals of the device 474 for each pressure-determined digital number that appears at the address terminals thereof will cause an oscillator 476, constructed as shown in FIG. 24, to produce an alternating signal having a frequency that is appropriate to the digitally expressed pressure at the input terminals of the encoder to cause the pump 40 to mimic the natural heart. Additionally, the encoder 472 comprises a second memory device 478, also preferably a type MM1702A PROM, that also receives the eight bit digital signal present at the data terminals of the memory device 474, such signal being supplied to the address terminals of the memory device 478 via a bus 480. In response to each digitally expressed signal received at the address terminals of the memory device 478, the memory device 478 produces a digitally expressed signal at the data terminals thereof and such digitally expressed signal is used to fix the amplitude of the signal supplied to the coils 438 and 440 in a manner that will be discussed below. In order to utilize the digitally expressed signals developed in the memory devices 474 and 478, the encoder further comprises D/A converters 475 and 479 which receive the outputs of the devices 474 and 478 respectively and output corresponding analog signals on conductors 525 and 549 respectively.

Referring now to FIG. 24, the oscillator 476 is comprised of a type XR2209 oscillator/timer 481 having resistors and capacitors connected to terminals thereof in a conventional manner, as shown, so that the oscillator/timer 481 will respond to a signal at a first terminal (manufacturers pin 4) and provide an alternating output at a second terminal (manufacturers pin 7) at a frequency proportional to the magnitude of the received signal. The first of these terminals is connected through a voltage divider to the conductor 525 and the second of these terminals is connected, via a conductor 483, to the clock terminal of a counter 485. Thus, the counter 485 continually runs through a sequence of numbers which are digitally expressed by voltage levels at a plurality of output terminals collectively indicated at 551 in FIGS. 24 and 25.

Figure 25:
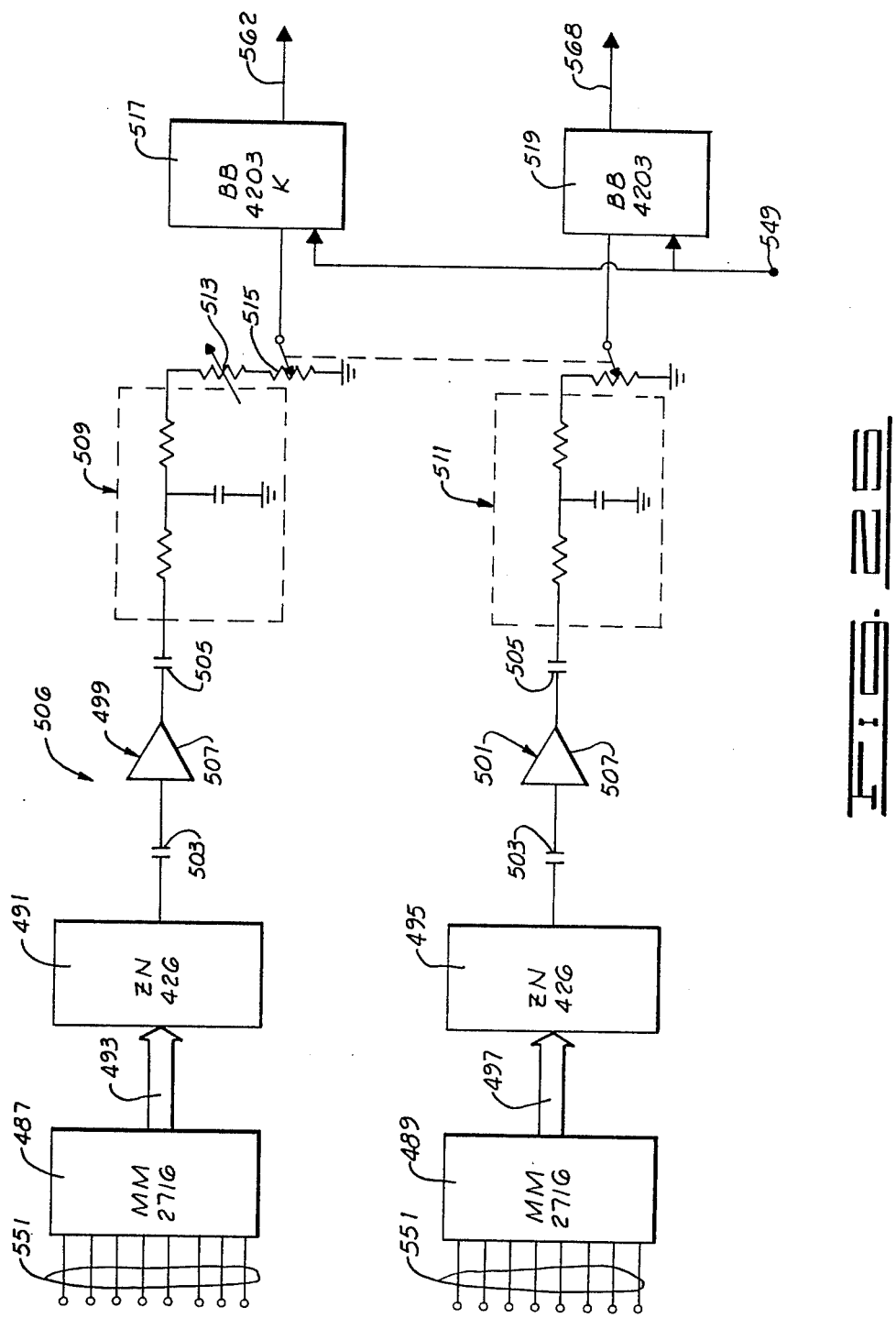
FIG. 25 is a circuit diagram of the modulator of the rotation control circuit shown in FIG. 22.

Referring now to FIG. 25, the terminals 551 are connected to the address terminals of two type MM2716 PROMS, 487 and 489, forming a part of a modulator 506 illustrated in FIG. 22. The PROM 487 is programmed with sequential values of the sine of an angle as the angle varies from 0° to 360° in steps equal to adjacent numbers appearing on the conductors 551 which form the bus 551 illustrated in FIG. 22. Thus, in response to one cycle of counts generated by the counter 485, the PROM 487 provides a sequence of values of the sine of an angle at its data terminals and such sequence of values are transmitted to a digital to analog converter 491 on a bus 493. The PROM 489 is similarly programmed to produce a sequence of values, defining the cosine of an angle from 0° to 360° in response to the counts appearing on the conductors 551 and such sequence is transmitted to a digital to analog converter 495 on a bus 497. Thus, the output of the D/A converter 491 is a stepwise generated sine function and the output D/A converter 495 is a stepwise generated cosine function. The outputs of the D/A converters 491 and 495 are passed through impedence matching circuits 499 and 501 respectively, each impedence matching circuit 499, 501 being comprised of two serially disposed capacitors 503 and 505 and an interposed operational amplifier 507, to identical low pass filters 509 and 511.

The output of the low pass filter 509 is passed to a variable resistor 513, used to balance the signal levels provided to the coils 438 and 440, and thence to one-half of a two section potentiometer 515. The other half of the potentiometer 515 receives the output of the low pass filter 511. The two wiper arms of the two sections of the potentiometer 515 are each provided to one input of a multiplier, the two multipliers being designated 517 and 519 in FIG. 25, and the second inputs of the multipliers 517 and 519 are connected to the conductors 549 of the encoder 472 shown in FIG. 23. Thus, the multipliers 517 and 519 produce, respectively, a sine wave output provided on an output conductor 562 and a cosine output provided on an output conductor 568 and such sine wave and cosine wave will have equal amplitudes that vary in accordance with the magnitude of the signal provided by the D/A converter 479.

Returning to FIG. 22, the conductor 562 is connected to the input terminal of a first power amplifier 564 and the conductor 568 is similarly connected to the input terminal of a second power amplifier 566. The output terminal of the first power amplifier 564 is connected to the terminal 450 of the drive coil 438 and the ouput terminal of the second power amplifier 566 is similarly connected to the terminal 454 of the second drive coil 440.

As will be clear from the above description of the rotor control circuit 458, the amplitude and frequency of the signal supplied to the coils 438 and 440 can be controlled to have any desired relationship to the measured value of any selected physical quantity. Once the frequency range has been selected and the sensor characterisitics have been determined, it is necessary only to program the PROM 474 to provide a digitally expressed value to the D/A converter 475 that will cause the oscillator/timer 481 to operate at a multiple of the desired frequency equal to the total range of numbers expressible on the conductors 551. Similarly, once the maximum desired amplitude of the drive currents for the coils 438 and 440 are known, along with the characteristics of the power amplifiers 564 and 566, it is necessary only to program the PROM 478 to provide, in conjunction with the D/A converter 479, an appropriate multiplying factor to the multipliers 517 and 519 on the conductor 549.

When the rotor suspension and rotation apparatus of the present invention is adapted to use as a blood pump, the capability of the rotor control circuit 548 to control both the amplitude and frequency of the signals supplied to the coils 438 and 440 in accordance with the pressure measured by the sensor 466 in the inlet passage 52 of the pump 40 is used to cause the pump 40 to mimic the natural heart, and to do so with minimum energy expenditure, as will now be described for the case in which the described eddy current drive system is used to rotate the impellor 42.

The Frank-Starling effect specifies both the pressure differential across the heart and the flow rate of blood through the heart for a range of blood pressure at the inlet of the heart so that, for each pressure in a known range, the flow rate and pressure differential the pump must produce to mimic the heart is known. In a centrifugal pump of the type shown in FIG. 1, the pressure differential is nearly independent of the flow rate, such pressure depending substantially only on the angular velocity of the impellor 42 of the pump 40. Additionally, maximum efficiency of operation of an eddy current motor, such as the motor incorporated into the pump 40, occurs when the operating point for the motor is slightly above a breakover peak in a plot of delivered torque versus rotor angular velocity for any selected amplitude and frequency of signals supplied to the stator of the motor. Thus, if the amplitude and frequency have selected values to provide an operating curve such as the curve 570 in FIG. 26, the maximum efficiency of operation will occur at the point 572. Similarly, if the amplitude and frequency are selected to provide the operating curve 574, or the curve 576, maximum efficiency of operation will occur at the point 578 or 580. As can be seen in FIG. 26, the angular velocity for which these maximum efficiency operating points occur are only slightly below angular velocities corresponding to synchronous operation of the eddy current motor. Thus, to a good approximation, the frequency at which power is to be supplied to the stator for any input pressure can be determined by measuring the angular velocity of the impellor for the pressure differential corresponding to the inlet pressure and dividing such angular velocity by 2 pi. By measuring the necessary angular velocity for a number of inlet pressure values within the range of pressures at the inlet to the human heart to achieve the pressure differential values given by the Frank-Starling effect corresponding to such pressure values, a number of frequencies of the signals to be supplied to the stators for a number of inlet pressures that might occur in the human heart are determined.

The Frank-Starling effect also provides the flow rate as a function of inlet pressure so that the total amount of work that must be done on the blood to achieve a given flow rate at a given pressure differential across a pump, such work being the product of the flow rate and the pressure differential, is also determined for each pump inlet pressure. This work is also the product of the impellor angular velocity and the delivered torque of the impellor so that the delivered torque is also determined for each inlet pressure. To find the necessary amplitudes of the signals to be supplied to the stators for each inlet pressure, the torque and angular velocity pairs for a number of inlet pressures are plotted on a graph such as shown in FIG. 26, as the points 572, 578 and 580, and the amplitudes of signals to be supplied to the stators to cause an operating curve at each of the frequencies determined for the selected inlet pressure points to pass through these points are experimentally determined. For example, the amplitude that yields the curve 570 passing through the point 572, at the frequency determined for the point 572 as described above for a given selected inlet pressure, is the amplitude at which the stator is to be driven for the selected pressure. By carrying out the procedure for several inlet pressures, a maximum efficiency curve 582 can be determined that is consistent with the Frank-Starling effect of the natural heart and the frequency and amplitude of the rotor drive signals corresponding to several points on the curve 582 will be known. The remaining amplitudes and frequencies corresponding to other pressures can then be determined by extrapolation along the curve 582. The amplitudes so determined are used to program the memory device 478 and the frequencies so determined are used to program the memory device 474.

Operation of the Rotor Suspension and Rotation Apparatus

While it is believed that the operation of the rotor suspension and rotation apparatus of the present invention will be clear from the above description of the pump 40 that includes such apparatus, in that such description includes the operation of each of the components of the pump 40, it will nevertheless be useful to briefly summarize the operation of the pump 40 as a whole beginning with the operation of the magnetic suspension assembly.

When the pump 40 is placed in operation, the housing magnets 74 and 76 will exert forces on the impellor magnets 78 and 80 that will cause the rotation axis 60 of the impellor 42 to align itself with the support axis 48 of the housing 44. However, the support for the impellor 42 provided by the permanent magnet impellor support assembly 68 is unstable with respect to axial movement of the impellor 42 along the housing support axis 48. Thus, in the absence of the stabilization that is provided by the electromagnet 70 and the electromagnet control circuit 72, the impellor 42 will move toward one of the inlet passages 52 and 54 until the impellor 42 engages one of the flared portions of the bore 46 that forms the impellor chamber 50. In the present invention, impellor 42 is maintained in a suspended position within the impellor chamber 50 as shown in FIG. 2 by forces that are exerted on the impellor magnets 78 and 80 by the electromagnet 70 to continually drive the impellor toward the control position in which the center of the impellor is either at or near the null position of the impellor which permanent magnet forces thereon cancel.

Initially, it will be useful to consider the case in which the only axial forces on the impellor are those provided by the permanent magnet impellor support assembly 68 and the electromagnet 70, the latter force being utilized only for stabilization purposes. If the impellor is initially at the null position, pulses of infrared radiation that are directed across the two inlet passages 52 and 54 by the light emitting diodes 158 and 160 will be equally shaded so that the phototransistors 170 and 172 of the infrared receivers 178 and 180 will be equally illuminated. Accordingly, each time the astable multivibrator 120 produces an electrical pulse to cause the light emitting diodes to direct an infrared pulse across the inlet passages 52 and 54, the infrared receivers 178 and 180 will deliver equal size electrical pulses to the difference amplifier 196 so that the output of the difference amplifier 196 will be zero for each pulse produced by the multivibrator 120. Between pulses, the light emitting diodes 158 and 160 do not emit so that the phototransistors 174 and 176 are not illuminated with the result that, between pulses, the difference amplifier receives no signals at its inputs and again produces no output. Thus, so long as the impellor 42 is located at the null position thereof, the difference amplifier will have a null output which is transmitted to the integrator 208. Thus, for each set of six pulses produced by the astable multivibrator to cause the integrator 208 to carry out an integration cycle, the integrator 208 will be receiving no input and will store no charge on the capacitor 216 thereof Thus, when the integrator 208 is connected to the sample and hold circuit by the closure of the switch 234 that has been described above, no charge will be transferred from the integrator to the sample and hold circuit so that the capacitor 232 of the sample and hold circuit will remain uncharged. Thus, the first controller 318 receives a null control signal which is matched by a null control signal provided by the summing circuit comprised of the resistors 336 and 338 with the result that the first controller 318 delivers a null signal to the power amplifier 322. In response to this null signal, the power amplifier 322 will pass no current through the electromagnet 70.

Should the impellor 42 now become displaced from the null position, the shading of one of the phototransistors 174, 176 by the impellor 42 will be increased while the shading of the other phototransistors 174, 176 will be decreased. Thus, with every electrical pulse produced by the astable multivibrator 120 to give rise to the pulses of infrared radiation directed across the passages 52, 54, unequal signals will reach the difference amplifier from the infrared receivers 178, 180 which include the phototransistors 170, 172 Thus, for every pulse produced by the astable multivibrator 120, the difference amplifier 196 will provide an electrical pulse to the integrator 208 and the magnitude and polarity of such pulse will depend upon the distance the impellor 42 has been shifted from the null position and the direction of such shift Four of every six of these pulses are integrated by the integrator 208 and, at the conclusion of such integration, the charge stored on the capacitor 216 of the integrator as the result of such integration is transferred to the sample and hold circuit 228. The charge that is transferred to the sample and hold circuit 228 is then stored therein and utilized to control the first controller for the next six pulses produced by the astable multivibrator 120. During the first two of these pulses, integrator 208 is reset to again integrate the signal from the difference amplifier 196 for the remaining four pulses immediately preceding the transfer of a new charge to the sample and hold circuit Thus, for every six electrical pulses produced by the astable multivibrator 120, the sample and hold circuit 228 will contain a charge, determined from the preceding four pulses produced by the astable multivibrator 120, that is indicative of the location of the impellor 42 with respect to the null position during such four preceding pulses. It will be noticed that the sample and hold circuit 228 stores a charge for a full six pulses rather than just the four pulses which produce the charge so that no time period occurs in which the sample and the hold circuit does not store a charge that is related to the position of the impellor 42 in the impellor chamber 50.

The sample and hold circuit 228 provides a signal proportional to the stored charge to the first controller 318 and the first controller 318 provides an output signal to the power amplifier 322 which is proportional to the difference between the signal received from the sample and hold circuit 228 and a signal received from the second controller 320. The second controller 320 is connected to the output of the first controller 318 and is adjusted via the variable resistor 366 thereof so that, in the absence of a persistent direct current component in the output of the first controller 318, the signal provided by the second controller 320 to the first controller 344 will be a null signal. Thus, so long as no persistent DC component arises in the output of the controller 318, the controller 318 will provide a signal to the power amplifier 322 which is indicative of the position of the impellor 42 with respect to the null position thereof. In response, the power amplifier 322 passes a current through the electromagnet 70 to produce a magnetic field that exerts a force on the impellor magnets 78 and 80 to drive the impellor back toward the null position in which the impellor 42 is centered in the impellor chamber 50.

Should an additional axial force now be exerted on the impellor 42, such force will cause the impellor 42 to shift away from the null position in the direction of the force so that unequal shading of the phototransistors 170 and 172, persistently in favor of one of the phototransistors, will occur. In the absence of the second controller, the electromagnet control circuit would operate as has been described above to pass a current through the electromagnet 70 tending to drive the impellor 42 back toward the null position. However, since the impellor 42 is now systematically displaced from the null position, the current passed through the electromagnet 70 will have a direct current component that will result in the large expenditure of energy by the electromagnet control circuit 72. The second controller 320 prevents this large expenditure of energy by detecting persistent signals in the output of the first controller 318 and, in response to the presence of such signals, providing a new reference signal to the first controller 318 against which the signal from the sample and hold circuit 228 is compared. Thus, the effect of the second controller 320 is to cause the first controller 318 to deliver a null signal to the power amplifier 322 for a condition in which the signal received by the first controller 318 from the sample and hold circuit 228 is not a null signal. In particular, the second controller 320 automatically causes the signal from the sample and hold circuit 228 for which the first controller output is a null signal to be the signal that is produced by the sample and hold circuit 228 when the impellor 42 is displaced from the null position to a control position at which the permanent magnet force on the impellor 42 just balances the additional axial force on the impellor 42. Thus, the electromagnet control circuit 72 and the electromagnet 70 maintain the impellor 42 at the control position which, in the absence of non-permanent magnet axial forces on the impellor 42, is the null position of the impellor 42 with the least expenditure of energy by the electromagnet control system 72 by using the permanent magnets of the permanent magnet impellor support assembly 68 to support the impellor 42 in the housing 44 while the current passed through the electromagnet 70 is used only for stabilization of the support of the impellor 42 within the housing 44.

In some applications of the magnetic suspension and rotation apparatus of the present invention, no static axial forces will be exerted on the suspended and rotated rotor other than the forces exerted thereon by the permanent magnet rotor support assembly 68. In these applications, the control position will coincide with the null position and the second controller 320 can be deleted from the electromagnet control circuit 72. The non-inverting input terminal of the operational amplifier 326 of the first controller 318 is connected directly to the wiper arm of the zero adjustment potentiometer 342 in such applications.

While the impellor 42 is so suspended, the pressure sensor 266, in the case of a blood pump, measures the fluid pressure in the first inlet passage 52 of the pump 40 and provides an analog signal proportional to such pressure to the A/D converter 468 which, in turn, provides a digitized representation of the magnitude of the pressure to the encoder 472. This representation is utilized in the memory device 474 to provide a code to the oscillator 476 that determines the frequency necessary to be supplied to the coils 438 and 440 disposed about the impellor 42 to form an eddy current motor with the shorting ring 424 that is mounted on the impellor 42 to cause, for a selected amplitude of the signal provided to the coils 438 and 440, the impellor 42 to rotate at a speed that will cause the flow of blood through the pump 40 to duplicate the flow rate of the natural heart at the pressure sensed by the sensor 466. The memory device 478 of the encoder 472 receives the output of the memory device 474 and is programmed to cause the modulator 506, which receives the oscillating signal produced by the oscillator 476, to provide the appropriate amplitude corresponding to such frequency so that, for each pressure sensed by the sensor 466, the flow rate of blood through the pump 40 will be the same as the flow rate produced by the natural heart for the same pressure at the inlet of the natural heart.

Description of FIGS. 27 and 28

FIGS. 27 and 28 illustrate a modification of the pump impellor, designated 42A in such Figures, that is particularly useful in high pressure pumping applications of a pump utilizing the magnetic rotor suspension and rotation apparatus of the present invention or in applications requiring a small size pump. The impellor 42A is comprised of an impellor body 570 that has the same form as the impellor 42; that is, the impellor 42A has first and second conical end portions, 572 and 574 respectively, that are joined at their bases in the same manner that the end portions 62 and 64 of the impellor 42 are joined. (The shorting ring and impellor magnets, not shown in FIGS. 27 and 28, are mounted on the impellor body 570 of the impellor 42A in the same manner and for the same purpose that the shorting ring 424 and impellor magnets 78, 80 are mounted on the impellor 42. Similarly, the impellor body 570 has a cavity that is symmetrically positioned with respect to the rotation axis 576 of the impellor 42A and with respect to a midplane at which the bases of the end portions 572 and 574 are joined so that the center of gravity of the impellor and portions of the suspension and rotor drive assemblies mounted thereon will be located at the center of buoyancy of the impellor 42A for the same reasons that have been discussed above with respect to the impellor 42.) In order to enable a pump comprising the impellor 42A to be utilized in high pressure pumping applications or to be made small without loss of pumping capacity, a plurality of curved vanes 578, only one of which has been numerically designated in the drawings, are disposed on each of the end portions of the impellor body 570 to extend generally from the center of the impellor body 570 to positions near the apices of the end portion 572 and 574 of the impellor body 570. The vanes 578 provide a stronger mechanical coupling between the rotor 42A than the viscous coupling provided by the surface of the rotor 42 so that a larger pressure differential can generally be established between the inlet and outlet passages of a pump containing the impellor 42A than can be established with a pump containing the impellor 42 or the same flow rate can be established in a smaller pump. In order to minimize damage to blood that might be occasioned by the vanes 578 should a pump including the impellor 42A be used in blood pumping operations, the vanes 578 are positioned along streamlines of blood through the pump for an average flow velocity of blood through the pump. Similarly, sharp edges are avoided on the vanes to prevent sharp stresses in the microenvironment of the blood components.

Description of FIG. 29

FIG. 29 illustrates a third embodiment of the impellor, designated 42B, that is also suitable for high pressure pumping applications of the magnetic rotor suspension and rotation apparatus of the present invention and for applications requiring minimum pump dimensions. The impellor 42B comprises an impellor body 580 that is hollow for specific gravity matching between the impellor 42B and a liquid pumped by the impellor 42B, the impellor body 580 having conical first and second end portions, 582 and 584 respectively, that are joined at their bases and have apices along the rotation axis 586 of the impellor 42D. In addition to the impellor body 580, the impellor 42B also includes two hollow, frusto-conical duct-forming shells 588 and 590 that are mounted on the impellor body 582 to extend coaxially about the end portions 582 and 584 respectively thereof. The coaxial disposition of the duct-forming members 588, 590 about the impellor body end portions 582, 584 forms ducts 592, 594 through the impellor 42B from the ends 596, 598 of the impellor 42B to the center of the impellor 42B such that the ducts 592, 594 extend about the impellor body 580 and open into the groove 58 (FIG. 3) that extends circumferentially about the impellor 42B when the impellor 42B is suspended in the housing 44. Webs 600 in the ducts 592, 594 are used to mount the duct-forming members 588 and 590 on the impellor body 580.

In the impellor 42B, the impellor magnets take the form of rings 602 and 604 that are mounted in the duct-forming members 588 and 590 respectively near the ends 596 and 598 of the impellor 42B. Like the impellor magnets 78 and 80 of the impellor 42, the impellor magnets 602 and 604 are axially magnetized; that is, magnetized parallel to the rotation axis 586 of the impellor 42B, to provide the same permanent magnet support for the impellor 42B that the impellor magnets 78 and 80 provide for the impellor 42. Additionally, the shorting ring, indicated at 606 in FIG. 29, that is used to convert the impellor 42B into the rotor of an eddy current motor, is mounted on the duct-forming members 588 and 590. In order to provide for the circumferenctial opening of the ducts 592 and 594 about the central portions of the circumference of the impellor 42B, the shorting ring 606 is constructed in two parts, indicated at 608 and 610 in FIG. 29, each of the parts 608 and 610 being mounted on one of the duct-forming members 588, 590 adjacent the circumferential opening of the ducts 592, 594 about the center of the impellor 42B.

The construction of the impellor 42B provides a stronger impellor-pumped fluid coupling by enhancing the viscous coupling between the impellor 42B and the liquid being pumped. That is, by forming the ducts 592, 594 through the impellor 42B, the impellor 42B presents a greater surface area in contact with the liquid than is presented by the impellor 42. Additionally, the webs 600 enhance the mechanical coupling between the impellor 42B and a liquid being pumped and the webs 600 can be curved along stream lines of liquid through the ducts 592, 594 for a selected angular velocity of the impellor 42B to limit mechanical working of the liquid when the impellor 42B is used in blood pumping applications Further enhanced mechanical coupling between the impellor 42B and liquid being pumped can be provided by vanes 612 on the radially outermost surface 614 of the duct-forming member 588 and vanes 616 on the radially outermost surface 618 of the duct-forming member 590. Curvature of the vanes 612 and 616 can similarly be used to limit mechanical damage to blood when the impellor 42B is used in blood pumping applications.

Description of FIG. 30

Referring now to FIG. 30, shown therein and designated by the reference numeral 42C is a fourth embodiment of an impellor suitable for use in pumping applications of the rotor suspension and rotation apparatus of the present invention. Like the impellor 42B, the impellor 42C is comprised of: a hollow impellor body 620, having first and second conical end portions 622 and 624 respectively that are joined at their bases and have apices along the rotation axis 626 of the impellor 42C; and hollow frusto-conical duct-forming shells 628 and 630 that are positioned coaxially about the end portions of the impellor body 620 to form annular ducts 632, 634 that extend from the ends 636, 638 of the impellor 42C to open circumferentially about the center of the impellor 42C. As in the case of the impellor 42B, the shorting ring 640 that extends about central portions of the impellor 42C to convert the impellor 42C into the rotor of an eddy current motor is constructed in two parts, 642 and 644, with one part being mounted on each of the duct-forming shells 628, 630. Similarly, in the impellor 42C, the impellor magnets 646, 648 have the form of axially magnetized rings that are mounted in the duct-forming shells 628 and 630 respectively.

In addition to the impellor body 620 and the duct-forming shells 628 and 630, the impellor 42C further comprises three hollow, frusto-conical intermediate shells 650–654 mounted in the duct 632 to extend coaxially about the first end portion 622 of the impellor body 620 and three hollow, frusto-conical shells 656-660 similarly mounted within the duct 634 to extend coaxially about the second end portion 624 of the impellor body 620. A web assembly 662 comprised of a plurality of webs (not numerically designated in the drawings) is used to mount the shells 628, 630 and 650-660 on the impellor body 620.

The impellor 42C has a large area in contact with a liquid being pumped by a pump including the impellor 42C to provide an enhanced viscous coupling between the impellor 42C and such liquid, thereby adapting the impellor 42C to high pressure pumping applications or, equivalently, to pumping applications in which the size of the pump is to be minimized.

Description of FIGS. 31 and 32

FIGS. 31 and 32 illustrate a second embodiment of a pump, generally designated by the numeral 664 in such Figures, that includes the magnetic rotor suspension and rotation apparatus of the present invention. The pump 664 comprises a housing 666 having a bore 668 formed therethrough and an impellor 670 mounted in central portions of the bore 668 to force a fluid axially through the bore 668. Thus, central portions of the bore 668 form an impellor chamber (not numerically designated in FIGS. 31 and 32) and end portions of the bore 668, intersecting ends 672 and 674 of the housing 666, form inlet and outlet passages 676 and 678 respectively, into the impellor chamber.

In the pump 664, the impellor 670 has the general form of a circular rod having tapered ends with the rotation axis (not designated in FIG. 31) of the impellor 670 extending longitudinally between the ends 680 and 682 of the impellor 670. In operation, the impellor 670 is supported along the axis 684 of the bore 668, the axis 684 forming the support axis of the housing 666 that is equivalent to the support axis 48 of the housing 40. The support of the impellor 670 is accomplished, in the same manner that the support of the impellor 42 is accomplished in the pump 40, via a permanent magnet impellor support assembly 686 that is comprised of two housing magnets 688 and 690 constructed, positioned, and magnetized in the manner of the housing magnets 74 and 76, and two ring-shaped, axially magnetized impellor magnets 692 and 694 that are positioned on the impellor 670 in relation to the positioning of the housing magnets 688, 690 in the same way that the impellor magnets 78 and 80 are positioned with respect to the housing magnets 74 and 76 in the pump 40. The permanent magnet impellor support assembly 686 thus tends to position the impellor 670 in the housing 666 in the same manner that the permanent magnet impellor support assembly 68 positions the impellor 42 in the housing 44 of the pump 40; that is, the permanent magnets 688-694 tend to align the rotation axis from the impellor 670 with the housing axis 684 while tending to drive the impellor 670 away from a magnetic null position located axially midway between the housing magnets 688 and 690 on the housing axis 684.

A plurality of vanes 696 are formed on the surface 698 of the impellor 670 to curve about the impellor 670 nearly the length thereof so that, when the impellor is rotated in the direction 700 indicated in FIG. 32, the impellor 670 will drive a liquid from the inlet passage 676 to the outlet passage 678 in the direction indicated by the arrows 702 and 704 in FIG. 31.

In order to stabilize the support of the impellor 670 provided by the permanent magnet impellor support assembly 686, the pump 664 includes an electromagnet 706, constructed and positioned substantially identically to the construction and position of the electromagnet 70 of the pump 40, and an electromagnet control circuit that is identical to the electromagnet control circuit 72. In order to mount the light emitting diodes 158 and 160 of the infrared transmitter 142 of the electromagnet control circuit 72 on the housing 666 of the pump 664, sockets 708 and 710 are formed in the inside wall of the housing 666 provided by the bore 668 and, similarly, in order to mount the phototransistors 174 of the two infrared receivers 178 and 180 on the housing 666, sockets 712 and 714 are formed coaxially with and in diametric opposition to the sockets 708 and 710. In the pump 664, a reaction force tending to drive the impellor 670 toward the end 672 of the housing 666 from which liquid enters the bore 668 will be exerted on the impellor 670 because of the axial nature of the flow of the liquid through the bore 668. This reaction force is countered, by the action of the second controller 320 that has been discussed above, by a shift in position of the impellor 670 to a control position which is slightly upstream of the null position at which the permanent magnet forces on the impellor 670 cancel.

Rotation of the impellor 670 is effected by a shorting ring 716 that extends about the center of the impellor 670 and a stator 718 mounted in the housing 666 to extend about the shorting ring 716. The stator 718 is comprised of a ferromagnetic ring 720 positioned concentrically with the shorting ring 716 and having four radially inwardly extending projections 722 formed thereon. A coil 723 is wound on two diametrically opposed projections 722 and a similar coil 724 is wound onto remaining two diametrically opposed projections 724 and the coils 723 and 724 are driven by a rotation control circuit that is identical to the rotation control circuit 458 shown in FIGS. 22-25. The mounting of the pressure sensor 466 of the rotation control circuit 458 in the pump 664 is via a socket 726 in the inlet passage 676 of the housing 666 as shown in FIG. 31.

The impellor 670 is formed symmetrically so that the center of gravity of the impellor and portions of the magnetic suspension assembly and impellor drive assembly mounted thereon will be located at the center of buoyancy of the impellor 670 and a cavity 729 is formed in the center of the impellor 670 to match the average specific gravity of the impellor 670 and portions of the magnetic suspension assembly and impellor drive assembly thereon to the specific gravity of the liquid that is pumped by the pump 664 for the reason that has been discussed above.

Figure 33:
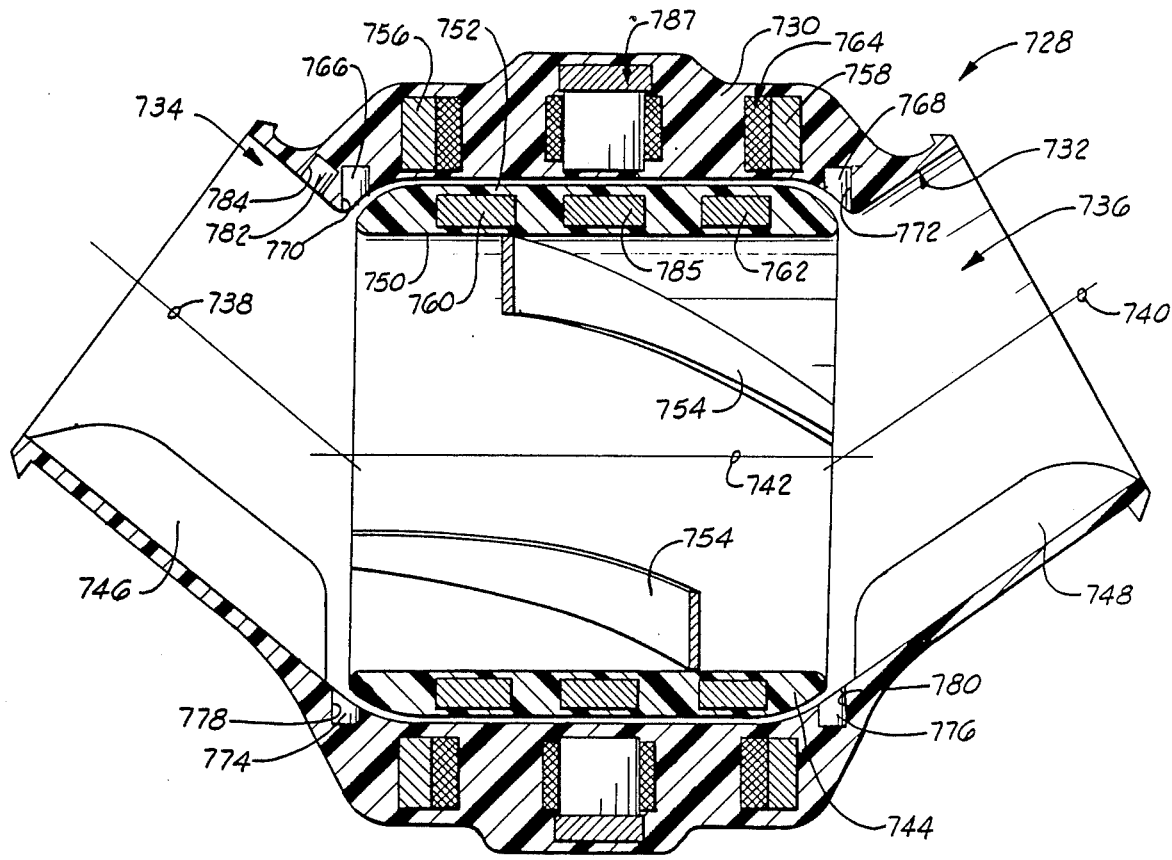
FIG. 33 is a cross section in side elevation of a third embodiment of a pump employing the magnetic rotor suspension and rotation apparatus of the present invention.

Description of FIG. 33

Referring now to FIG. 33, shown therein and designated by the numeral 728, is another embodiment of a pump constructed in accordance with the present invention to include a magnetic rotor suspension and rotation apparatus. The pump 728 comprises a housing 730 that is similar to the housing 666 of the pump 664, housings 630 and 666 differing primarily in the manner in which a bore 732 is formed through the housing 730 and in the addition of flow control structures in the bore 732. In the housing 730, the portions of the bore 732 that form an inlet passage 734 and outlet passage 736 to, and from, the central portion of the bore 732 that forms an impellor chamber are formed, respectively, about an inlet flow axis 738 and an outlet flow axis 740 that are not coincident with the housing support axis 742 along which the rotation axis of the pump impellor (not numerically indicated in FIG. 33), extends. Rather, the inlet flow axis 738 and the outlet flow axis 740 each intersect the housing support axis 742 at an obtuse angle so that the inlet and outlet passages 734 and 736 are both canted to one side of the housing 730, such side being the same for both passages 734 and 736. The canting of the inlet and outlet passages 734 and 736 respectively provides the pump 728 with a shape that is similar to the shape of the human heart to facilitate positioning of the pump 728 within the chest and further tends to eliminate formation of vortical flow patterns in a fluid pumped by the pump 728 to thus reduce the energy required to rotate the impellor 742. Vortical flow suppression is also affected by a flow control vane 746 that is formed integrally with the housing 730 within the inlet passage 734 parallel to the inlet flow axis 738 and an outlet flow control vane 748 formed integrally with the housing 730 within the outlet passage 736 to parallel the outlet flow axis 738.

The impellor 744 in the pump 728 differs from the impellor 670 of the pump 664 in that the impellor 744 has the form of a circular ring having coaxial inner and outer peripheral surfaces, 750 and 752 respectively, centered on the rotation axis (not numerically designated in FIG. 33) of the impellor 744. A plurality of curved vanes 754 are formed integrally with the impellor 744, on the inner peripheral surface 750 thereof, so that a fluid can be forced through the pump 728, from the inlet passage 734 to the outlet passage 736, by rotating the impellor 744 about the rotation axis thereof.

The pump 728 is provided with a magnetic suspension assembly that is identical to the magnetic suspension assembly of the pump 664 so that such magnetic suspension assembly need not be again described herein. Rather, it will suffice to numerically identify the portions of the magnetic suspension assembly that are mounted on the housing and impellor of the pump 728. Such portions of the magnetic suspension assembly for the pump 728 are: ring shaped permanent housing magnets 756 and 758; ring shaped permanent impellor magnets 760 and 762; an electromagnet 764; two light emitting diodes 766 and 768 disposed in sockets 770 and 772 respectively at opposite ends of the impellor chamber; and two phototransistors 774 and 776 disposed in sockets 778 and 780 that are coaxially with, and in diametric opposition across the impellor chamber to, the sockets 770 and 772.

The rotation rate of the impellor 744 can be controlled in relation to the pressure at the inlet passage 734 of the pump 728 in accordance with the Frank-Starling effect and a pressure sensor 782 is mounted in a socket 784 formed in the wall of the inlet passage 734 for this purpose. The rotation of the impellor 744 is then effected via a shorting ring 785 mounted on the impellor 744 to extend about central portions thereof and a stator 787 that is identical to the stator 718 of the pump 664 shown in FIG. 31. Control of the rotation rate of the impellor 744 so that the pumping rate of the pump 728 will mimic the pumping characteristics of the natural heart is then effected with a rotor control circuit such as the rotor control circuit 458 shown in FIGS. 22-25.

Figure 34:
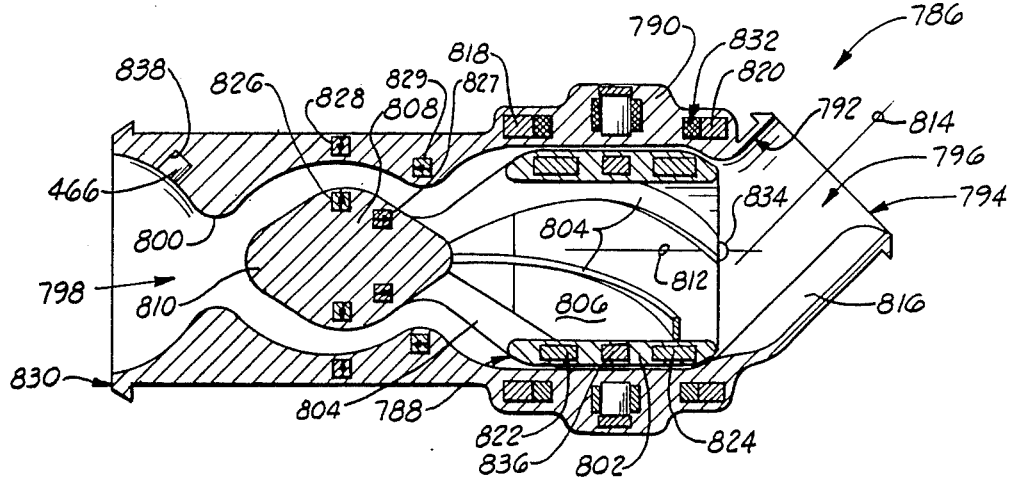
FIG. 34 is a cross section in side elevation of a fourth embodiment of a pump employing the magnetic rotor suspension and rotation apparatus of the present invention.

Description of FIG. 34

FIG. 34 illustrates another embodiment of a pump, designated by the general reference numeral 786, that has an impellor 788 suspended and rotated by the magnetic rotor suspension and rotation apparatus constructed in accordance with the present invention. The pump 786 is particularly suited for use as a heart assist device.

The pump 786 is comprised of a housing 790, having a bore 792 formed therethrough, and portions of the bore 792 near one end 794 of the housing 790 provide an impellor chamber (not numerically designated in FIG. 34) in which the impellor 788 is disposed. In particular, the impellor 788 is displaced generally from central portions of the bore 792 toward the end of the housing 790 that is intersected by the outlet passage 796 of the pump 786. The portion of the bore 792 forming an inlet passage 788 is elongated and an annular restriction 800 is formed in the inlet passage 798 to provide part of a valve that automatically closes the bore 792 should the pump 786 cease to operate for some unforseeable reason. Thus, where the pump 786 is used as a heart assist device, as will be discussed below, a cessation of the operation of the pump 786 will not result in a back flow through the bore 792 as the heart continues to beat.

The impellor 788 in the pump 786 has a ring-shaped portion 802 that is substantially identical to the impellor 744 of the pump 728 and curved vanes 804 formed integrally with the portion 802 on the inner peripheral surface 806 of such portion 802 effect the pumping of liquid through the portion 802 in response to rotation of the impellor 788 about a rotation axis extending axially through the impellor 788 along the center of the ring shaped portion 802. The vanes 804 extend axially from the portion 802 of the impellor 788 to support a valve member 808 adjacent the annular restriction 800 formed in the inlet passage 798 and the valve member 808 has a nose portion 810 that is shaped to mate with the restriction 800 so that, should the pump 786 cease to operate at a time that the pump 786 is assisting a natural heart, blood pressure exerted by the heart will force the nose portion 810 of the valve member 808 into the restriction 800 to prevent back flow through the pump 786.

In order to accomodate the automatic valve provided by the restriction 800 and the valve member 808, the inlet passage 798 of the valve 786 extends axially from the impellor chamber in which the ring shaped portion 802 of the impellor 788 is disposed; that is, the inlet passage 798 is formed about the housing support axis 812 shown in FIG. 34. The outlet passage 796, however, is preferably canted with respect to the housing support axis in the manner that the outlet passage 736 is canted and for the same reasons. Thus, the outlet passage 792 is centered on an outlet flow axis 814 that makes an obtuse angle with the housing support axis 812. Similarly, an outlet flow control vane 816 is integrally formed with the housing 790 to extend axially through the outlet passage 796 parallel to the outlet flow axis 814.

The magnetic suspension assembly for the pump 786 differs from the magnetic suspension assembly for the pump 728 in several respects. In addition to the inclusion in the pump 786 of permanent housing magnets 818 and 820 and permanent impellor magnets 822 and 824, which are shaped, positioned, and magnetized in a manner identical to the shaping, positioning and magnetization of the magnets 756-762 of the pump 728, the pump 786 also comprises ring-shaped impellor magnets 826 and 827 that are mounted in the valve member 808 and ring-shaped housing magnets 828 and 829 that are mounted in the housing 790 to extend about the inlet passage 798. As indicated in FIG. 34, the magnets 826 and 828 are disposed concentrically and are radially magnetized in opposite directions to provide stable radial support of the valve member 808 and unstable axial support. The magnets 827 and 829 are axially magnetized in opposite directions, as shown, and are positioned and dimensioned to provide a small axial force on the impellor 788 tending to drive the valve member 808 into the restriction 800. Thus, should the pump 786 cease to operate, the magnets 827 and 829 will reinforce the tendency of the magnets 808-824 to automatically close the inlet 798 of the pump 786 to prevent the formation of short circuit between the inlet and outlet of the natural heart with which the pump 786 might be used.

Because of the shape of the impellor 788 of the pump 786, it is convenient to use a modified electromagnet control circuit that includes only one infrared receiver and for which the infrared transmitter includes only one light emitting diode, such light emitting diode, indicated at 834 in FIG. 34, being positioned in the housing 790 adjacent the outlet passage 792. (The infrared receiver that is included in the electromagnet control circuit provided for the pump 786 will include a phototransistor that has not been shown in FIG. 34 but is positioned in diametric opposition to the light emitting diode 834 in the manner of phototransistors and light emitting diodes in previously described embodiments of pumps that incorporate the magnetic impellor suspension and rotation apparatus of the present invention.) When only one infrared receiver is utilized in the stabilization of the support of an impellor, or rotor, that is suspended in accordance with the principles of the present invention, the conductor 194 in FIG. 12 leading to the inverting input of the operational amplifier 198 of the difference amplifier of the electromagnet control circuit is connected to the circuit ground for the electromagnet control circuit and the zero adjustment potentiometer 342 in the first controller shown in FIG. 16 is adjusted so that the signal at the output terminal of the difference amplifier 326 of the first controller 318 will be zero when the impellor, or rotor, being stabilized is at the null position thereof in the absence of axial forces on the impellor, or rotor, not arising from permanent magnets used to support such impellor or rotor.

The impellor 788 can be rotated via a shorting ring 836 mounted in the impellor 788, a stator (not numerically designated in FIG. 34) mounted in the housing 790 in the same manner that the stator 718 in FIG. 32 is mounted in the housing 666 of the pump 664, and a rotor control circuit that is identical to the rotor control circuit 458 shown in FIGS. 22-25. To provide for the control of the rotation speed of the impellor 788 of the pump 786, a socket 838 is formed in the wall of the inlet passage 798 to receive the pressure sensor 466 of such rotor control circuit 458.

Figure 35:
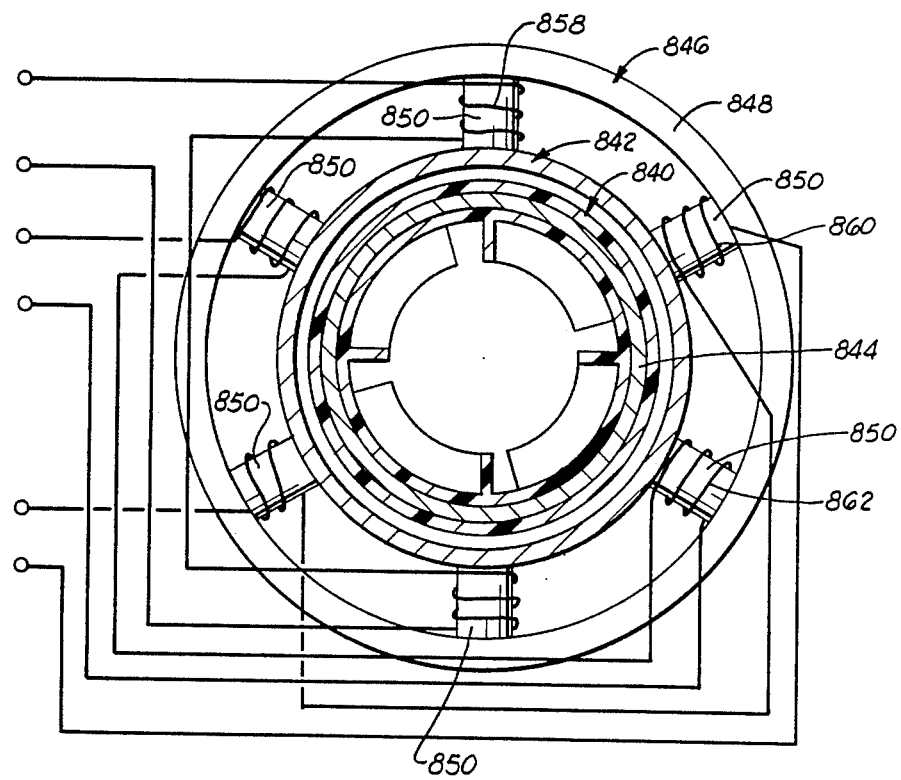
FIG. 35 is a cross section in end elevation of a second preferred arrangement of stator coils in a pump employing the magnetic rotor suspension and rotation apparatus of the present invention and particularly adapted for use in the pumps illustrated in FIGS. 31-34.

Description of FIGS. 35 and 36

FIGS. 35 and 36 illustrate a second embodiment of a rotor drive assembly that can be used to rotate a rotor or impellor that is magnetically suspended in accordance with the principles of the present invention. In FIG. 35, the impellor has been designated by the numeral 840 and FIG. 35 contemplates that the impellor 840 will be magnetically suspended within a housing 842 and rotated via an eddy current drive in a manner similar to the rotation of the impellors that have been previously discussed. Thus, a shorting ring 844 is included in the impellor 840 to extend about central portions of the impellor 840. However, instead of comprising a stator having four radially inwardly directed projections on a ring portion concentric with the shorting ring as previously discussed, the rotor drive assembly illustrated in FIGS. 35 and 36 is comprised of a stator 846 that includes a ring 848 positioned concentrically with the shorting ring 844 and having six equally spaced, radially inwardly extending projections 850. Windings 858, 860 and 862 are each wrapped on one pair of diametrically opposed projections 850 and a modified rotor control circuit is used to pass currents through the stator windings 858-862.

Initially, in order to provide an eddy current drive with three stator windings, the windings are connected together in a star connection as indicated by the connection of each of the windings 858-862 to the grounded conductor 864 in FIG. 36. The stator windings are then driven by oscillating signals having the same amplitudes and frequencies but out of phase, from one stator winding to the next, by 60°. In FIG. 36, these signals are provided by power amplifiers 866-870 that are connected to the three stator windings 858-862 respectively and are constructed in the manner of the power stage 372 of the power amplifier 322 of the suspension circuit 72. As in the case of the rotor control circuit 458, each of the power amplifiers 866-870 is driven by a modulator that is constructed in the manner shown in FIG. 25, such modulators being indicated for the power amplifiers 866-870 at 872-876 respectively in FIG. 36. Thus, the rotation of the impellor 840 in FIG. 35, and the control of such rotation in accordance with a preselected relationship between the angular velocity of the impellor 840 and the value of a measured physical quantity, can be achieved by supplying an appropriate, digitally expressed amplitude control signal to the multiplying A/D convertor of each of the modulators 872-876, via buses 878-882 shown in FIG. 36, and by supplying appropriately phased oscillating signals to the reference input terminals of the convertors of the modulators 872-876 on conducting paths 884-888 shown in FIG. 36.

The supply of digitally expressed amplitude control signals to the modulators 872-876 is effected in the same manner that amplitude control signals are supplied to the modulators 506 and 508 of the rotor control circuit 458. That is, the amplitude control signals are supplied on the buses 878-882 directly from an encoder (not shown in FIG. 36 but having the same form as the encoder 472 shown in FIG. 23) that receives signals from a sensor (not shown in FIG. 36) via an A/D convertor (not shown in FIG. 36). The encoder used to supply these amplitude control signals is also used to fix the frequency of oscillation of an oscillator (not shown in FIG. 36 but constructed in the manner of the oscillator 476 shown in FIG. 24) from which the alternating signals on the conducting paths 884-888 are derived as will now be discussed.

One output of the oscillator from which the signals on the paths 884-888 are derived is connected, via a conductor 890, to the clock terminal (not shown) of a binary counter 892, having a plurality of output terminals (not shown) at which a binary number can be expressed as a pattern of high and low voltages, so that the binary number at the output terminals of the counter 892 is incremented for each cycle of the signal received on the path 890. The output terminals of the counter 892 are connected, via buses 894-898, to three function storage devices indicated at 900-904 in FIG. 36. The function storage devices 900-904 are conveniently PROMS to the address terminals of which are connected the buses 894-898 respectively. The function storage devices 900-904 are programmed to provide, at data terminals thereof, a sequence of values in one cycle of a sine curve in response to one complete cycle of binary numbers produced by the counter 892, the sequence of values of the sine curve being divided into a number of equal increments that is equal to the maximum number of values that can be expressed as a binary number at the output terminals of the counter 892. Thus, the binary numbers at the data terminals of the function storage devices 900-904 will run through a sequence of values of a sine curve each time the counter 892 runs through a complete cycle of numbers beginning with all output terminals of the counter 892 being at a low voltage and ending with all output terminals of the counter 892 being at a high voltage. Moreover, the programming of the function storage devices 900-904 is correlated so that the first number appearing at the data terminals of the function storage device 900 as the counter 892 runs through one complete cycle beginning with the binarily expressed number 0 is the sine of 0°; the first number to appear at the data terminals of the function storage device 902 as the counter 892 runs through a cycle is the binary expression of the sine of 60°; and the first number to appear at the data terminals of the function storage device 904 as the counter 892 runs through a cycle is the binary expression of the sine of 120°. Thus, each time the counter 892 runs through one complete cycle of numbers beginning with a binarily expressed 0, the function storage devices 900-904 will run through a series of numbers corresponding to equal increments in the functions sin (360° n/N), sin (360° n/N+60°), and sin (360° n/n+120°) where n is the number expressed at the output terminals of the counter 892 and N is the maximum number expressible by the counter 892. The data terminals of the function storage devices 900-904 are connected to the inputs of D/A convertors 906-910 respectively via buses 912-916 respectively so that step wise approximations of the functions sin X, sin (X+60°), and sin (X+120°) are produced at output terminals (not shown) of the D/A convertors 906-910 each time the counter 892 runs through one complete cycle of numbers beginning with a binarily expressed 0. The outputs of the D/A convertors 906-910 are provided, on signal paths 924-928 respectively, to filters 918-922 respectively and the outputs of the filters are supplied on the signal paths 884-888 to the modulators 872-876. Thus, the reference input terminals of the multiplying D/A convertors of the modulators 872-876 are supplied with sine wave signals having the same amplitudes and frequencies but out of phase by 60° from one signal to another to provide appropriate signals for driving the stator windings 858-862 to cause eddy currents in the shorting ring 844 to rotate the impellor 840.

Figure 37:
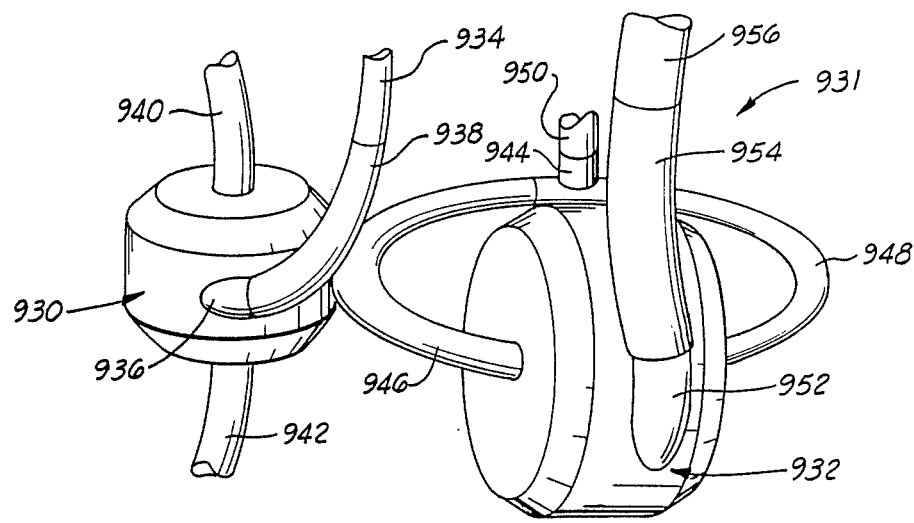
FIG. 37 is an isometric view of two pumps employing the apparatus of the present invention illustrating the use of such pumps as an artificial heart.

Description of FIG. 37

FIG. 37 has been included to indicate, schematically, the manner in which an artificial heart, designated by the numeral 931, can be assembled using pumps including the magnetic rotor suspension and rotation apparatus of the present invention and connected into the circulatory system of a human patient. For such application of the invention, two pumps, 930 and 932, are used, each of the pumps 930 and 932 having its own magnetic suspension assembly and its own impellor drive assembly constructed as has been discussed above. One power supply, comprised of a plurality of rechargeable batteries, implanted in the body along with the pumps 930, 932, can be used to operate both pumps and it is contemplated that the batteries of the power supply can be periodically recharged via an induction coil implanted in the body as disclosed in the aforementioned U.S. Pat. application, Ser. No. 245,007.

The pumps 930 and 932 can be pumps of the type illustrated in FIGS. 1-3 and an advantage of the use of such pumps is the capability such pumps provide for matching the average specific gravity of the impellors of the pumps to the specific gravity of blood as discussed above. With such matching, and the construction of the pump impellors so that the centers of gravity of the pump impellors are located at the centers of buoyancy of the impellors, and the impellors of the pumps 930, 932 are effectively portions of the blood being pumped insofar as gravitational and buoyant forces are concerned and insofar as inertial effects arising from accelerations of the pumps 930 and 932 are concerned. Thus, no work need be done by the magnetic suspension assembly as the result of movements of the person receiving an artificial heart comprised of the pumps 930 and 932. Moreover, the energy required to operate the pumps 930 and 932 is completely independent of the orientations of the pumps 930, 932 in the chest cavity so that geometrical considerations such as the attachment of the pumps 930, 932 to the circulatory system and the fitting of the pumps 930, 932 in the position normally occupied by the heart can control the positioning of the pumps 930, 932 in the body. Convenient orientations of the pumps have been shown in FIG. 37.

In the use of two pumps, such as the pumps 930 and 932, as an artificial heart, the pumps can be of different sizes and different power capabilities corresponding to the different sizes and pumping capabilities of the two sides of the heart. Such differences have been contemplated in FIG. 32 in which the pump 930 is illustrated as being smaller than the pump 932. In this case, the smaller pump 930 is utilized to provide a flow of blood into the pulmonary artery 934 to which the outlet 936 of the pump 930 is connected via a length of tubing 938 constructed of a plastic that is compatible with blood. The two inlets of the pump 930 are inserted into, and secured to, the superior vena cava 940 and the inferior vena cava 942 so that the pump 930 occupies a position normally occupied by the right atrium of the natural heart. The pump 932 is positioned at the location normally occupied by the ventricles of the heart and the inlets of the pump 932 are connected to a T-fitting 944 via tubes 946 and 948. FIG. 37 contemplates that the left atrium of the natural heart will be left in the chest cavity of the person receiving the artificial heart and the T-fitting 944 is connected to the left atrium by means of a length of tubing 950. The outlet 952 of the pump 932 is attached, either directly or via a length of tubing 954, to the aorta of the person receiving the artificial heart. (For clarity of illustration, the artificial heart 931 has been illustrated schematically such that the pumps 930 and 932 comprising the heart 931 are separated from each other. As will be clear to one skilled in the art, the pumps 930 and 932 would be placed in close proximity when implanted in the chest cavity of a person receiving the artificial heart 931.)

Figure 38:
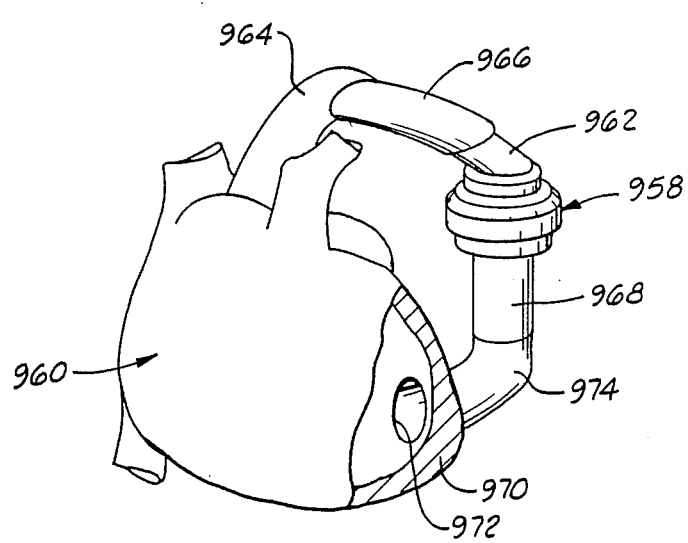
FIG. 38 is an isometric view of a pump constructed in the manner shown in FIG. 34 illustrating the use of such pump as an assist to the natural heart.

Description of FIG. 38

Referring now to FIG. 38, shown therein is one preferred manner in which a pump 958, constructed in the manner of the pump 786 illustrated in FIG. 34, is connected to the natural heart 960 to operate as a left ventricular assist device. Such attachment is effected by connecting the outlet 962 of the pump 958 to the arch of the aorta 964, via a length of tubing 966, and by connecting the inlet 968 of the pump 958 to the left ventricle 970 of the heart 960. For this latter connection, a hole 972 would be formed through the wall of the left ventricle so that a length of tubing 974 could be sewn to the heart 960 to open into the left ventricle and the tubing 974 would be slipped over the inlet 968 of the pump 958 and secured thereto. Alternatively, the tube 974 can be similarly sewn to the left atrium.

Although not shown in the Figures, each blood-contacting surface in the apparatus is preferably provided with a continuous, substantially inert coating, such as that formed by a non-solvent material. One preferred coating comprises pyrolitic carbon. Among the surfaces which are coated are the exterior surface of the rotor and the internal bore of the housing. If desired, non-blood-contacting surfaces, such as the outside of the housing, may also be coated. The coating protects operative components of the apparatus and, because of its inertness, permits greater flexibility in selection of the structural materials from which blood-contacting components are formed. By using a non-solvent material, it is possible to avoid problems of coating degradation, which are often associated with coatings formed by solution-cast processes.

It is clear that the present invention is well adapted to carry out the object and attain the ends and advantages mentioned as well as those inherent therein. While presently preferred embodiments of the invention have been described for purposes of this disclosure, numerous changes may be made which will readily suggest themselves to those skilled in the art and which are encompassed within the spirit of the invention disclosed and as defined in the appended claims.

What is claimed is:

1. A pump implantable in the human body to provide a replacement for, or an assist to, the natural heart, comprising:
    a housing constructed of or coated with a blood compatible material having an inlet passage and an outlet passage for connecting the pump into the circulatory system of the person into which the pump is implanted, the housing having an impellor chamber fluidly interposed between the inlet passage and the outlet passage;
    an impellor constructed of or coated with a blood compatible material disposed in the housing impellor chamber and rotatable therein about an impellor rotation axis for drawing blood into the housing inlet passage and discharging blood from the housing outlet passage;
    magnetic suspension means for magnetically suspending the rotor in said pump chamber out of contact with the walls of the impellor chamber, comprising:
        permanent magnet impellor support means comprising an assembly of permanent magnets mounted on the impellor and on the housing for exerting forces on the impellor tending to align the rotation axis of the impellor with a selected support axis of the housing while tending to drive the impellor axially away from a selected null position on said support axis at such times that the impellor is axially displaced from the null position;
        an electromagnet mounted on the housing and positioned thereon to exert a force directed along the support axis on portions of the permanent magnet impellor support means disposed on the impellor at such times that an electric current is passed through the electromagnet, the electromagnet thereby exerting an axial force on the rotor,
        electromagnet control means mounted on the housing for detecting a displacement of the impellor from a control position of the impellor on the support axis and passing a current through the electromagnet to drive the impellor toward the control position; and
        impellor drive means mounted on the housing for sensing a preselected physical quantity related to the flow of blood in said circulatory system and magnetically coupled to the impellor for rotating the impellor at a rate varying in accordance with a selected relationship to the value of said quantity.

2. The pump of claim 1 wherein said physical quantity is the pressure in the inlet passage of the housing.

3. The pump of claim 2 wherein the impellor chamber, the inlet passage and the outlet passage are characterized as being portions of a bore formed through the housing; wherein an annular restriction is formed in the inlet passage of the pump; and wherein the pump further comprises a valve member mounted on the impellor adjacent said restriction, the valve member having a nose portion shaped to mate with said restriction whereby the inlet passage of the housing can be closed by movement of the valve member nose portion into said restriction.

4. The pump of claim 1 wherein said control position is coincident with said null position.

5. The pump of claim 1 wherein the electromagnet control means is characterized as comprising means for selecting the control position in a displaced relation to the null position along said support axis, whereby the permanent magnet rotor support means will exert a force on the rotor at such times that the rotor is in the control position, thereby enabling the permanent magnets of the permanent magnet impellor support means to balance a static force exerted axially on the rotor.

6. The apparatus of claim 1 in which blood-contacting surfaces of the housing and rotor are each provided with a non-solvent coating.

7. An artificial heart for implantation in the body of a human subject comprising:
    a first pump comprising a housing constructed of or coated with a blood compatible material having an inlet passage fluidly connectable to the subject's left atrium and an outlet passage fluidly connectable to the subject'aorta; and
    a second pump comprising a housing constructed of or coated with a blood compatible material having an inlet passage connectable to at least one of the subject's superior vena cava and inferior vena cava and an outlet passage fluidly connectable to the subject's pulmonary artery;
    wherein the housing of each of said pumps has an impellor chamber disposed between the housing inlet passage and the housing outlet passage; and wherein each of said pumps further comprises:

an impellor disposed in the housing impellor chamber and rotatable therein about an impellor rotation axis for drawing blood from the housing outlet passage;

magnetic suspension means disposed partially on the impellor and partially on the housing for magnetically suspending the impellor in said impellor chamber out of contact with the walls of the pump chamber, comprising:

permanent magnet impellor means comprising an assembly of permanent magnets mounted on the impellor and on the housing for exerting forces on the impellor tending to align the rotation axis of the impellor with a selcted support axis of the housing while tending to drive the impellor axially away from a selected null position on said support axis at such times that the impellor is axially displaced from the null position;

an electromagnet mounted on the housing and positioned thereon to exert a force directed along the support axis on portions of the permanent magnet impellor support means disposed on the impellor at such times that an electric current is passed through the electromagnet, the electromagnet thereby exerting an axial force on the rotor; and electromagnet control means mounted on the housing for detecting a displacement of the impellor from a control position of the impellor on the support axis and passing a current through the electromagnet to drive the impellor toward the control position; and impellor drive means disposed partially on the impellor and partially on the housing for turning the impellor about said rotation axis, wherein portions of the impellor drive means disposed on the impellor are coupled solely magnetically to portions of the impellor drive means disposed on the housing.

8. The apparatus of claim 7 in which blood-contacting surfaces of the housing and rotor are each provided with a non-solvent coating.

9. A pump for pumping blood implantable in the human body to provide a replacement for, or an assist to, the natural heart, comprising:

a housing constructed of or coated with a blood compatible material having an inlet passage and an outlet passage for connecting the pump into the circulatory system of the person into which the pump is implanted, the housing having an impellor chamber fluidly interposed between the inlet passage and the outlet passage;

an impellor constructed of or coated with a blood compatible material disposed in the housing impellor chamber and rotatable therein about an impellor rotation axis for drawing blood into the housing inlet passage and discharging blood from the housing outlet passage;

magnetic suspension means for magnetically suspending the rotor in said pump chamber out of contact with the walls of the impellor chamber, comprising:

permanent magnet impellor support means comprising an assembly of permanent magnets mounted on the impellor and on the housing for exerting forces on the impellor tending to align the rotation axis of the impellor with a selected support axis of the housing while tending to drive the impellor axially away from a selected null position on said support axis at such times that the impellor is axially displaced from the null position;

an electromagnet mounted on the housing and positioned thereon to exert a force directed along the support axis on portions of the permanent magnet impellor support means disposed on the impellor at such times that an electric current is passed through the electromagnet, the electromagnet thereby exerting an axial force on the rotor.

electromagnet control means mounted on the housing for detecting a displacement of the impellor from a control position of the impellor on the support axis and passing a current through the electromagnet to drive the impellor toward the control position;

impellor drive means mounted on the housing for sensing the pressure in the inlet passage of the housing related to the flow of blood in the circulatory system and magnetically coupled to the impellor for rotating the impellor at a rate varying in accordance with a selected relationship to the value of the pressure in the inlet passage of the housing; and wherein the combined center of gravity of the impellor and portions of the impellor drive means and permanent magnet impellor support means disposed thereon is positioned at the center of buoyancy of the impellor, and wherein a cavity is formed in the impellor to match the average specific gravity of the impellor and portions of the drive means and the permanent magnet impellor support means thereon to the specific gravity of blood.

10. A pump implantable in the human body to provide a replacement for, or an assist to, the natural heart, comprising:

a housing constructed of or coated with a blood compatible material having an inlet passage and an outlet passage for connecting the pump into the circulatory system of the person into which the pump is implanted, the housing having an impellor chamber fluidly interposed between the inlet passage and the outlet passage;

an impellor constructed of or coated with a blood compatible material disposed in the housing impellor chamber and rotatable therein about an impellor rotation axis for drawing blood into the housing inlet passage and discharging blood from the housing outlet passage;

magnetic suspension means for magnetically suspending the rotor in said pump chamber out of contact with the walls of the impellor chamber, comprising:

permanent magnet impellor support means comprising an assembly of permanent magnets mounted on the impellor and on the housing for exerting forces on the impellor tending to align the rotation axis of the impellor with a selected support axis of the housing while tending to drive the impellor axially away from a selected null position on said support axis at such times that the impellor is axially displaced from the null position;

an electromagnet mounted on the housing and positioned thereon to exert a force directed along the support axis on portions of the permanent magnet impellor support means disposed on the impellor at such times that an electric current is passed through the electromagnet, the electromagnet thereby exerting an axial force on the rotor, electromagnet control means mounted on the housing for detecting a displacement of the impellor from a control position of the impellor on the support axis and passing a current through the electromagnet to drive the impellor toward the control position; comprising:

means for selecting the control position in a displaced relationship to the null position along said support axis, whereby the permanent magnet impellor support means will exert a force on the impellor at such times that the impellor is in the control position, thereby enabling the permanent magnets of the permanent magnet impellor support means to balance a static force exerted axially on the impellor;

impellor drive means mounted on the housing for sensing a preselected physical quantity related to the flow of blood in said circulatory system and magnetically coupled to the impellor for rotating the impellor at a rate varying in accordance with a selected relationship to the value of said quantity; and wherein the combined center of gravity of the impellor and portions of the impellor drive means and permanent magnet impellor support means disposed thereon is positioned at the center of buoyancy of the impellor, and wherein a cavity is formed in the impellor to match the average specific gravity of the impellor and portions of the drive means and the permanent magnet impellor support means thereon to the specific gravity of blood.

* * * * *

UNITED STATES PATENT AND TRADEMARK OFFICE
CERTIFICATE OF CORRECTION

PATENT NO. : 4,944,748
DATED : July 31, 1990
INVENTOR(S) : Bramm, et. al.

It is certified that error appears in the above-indentified patent and that said Letters Patent is hereby corrected as shown below:

Column 47, line 10, after the word, impellor, the word --support-- should be added.

Column 47, line 14, "selcted" should be --selected--.

Signed and Sealed this

Fifth Day of July, 1994

Attest:

BRUCE LEHMAN

Attesting Officer

Commissioner of Patents and Trademarks